(12) United States Patent
Heinz et al.

(10) Patent No.: US 10,822,605 B2
(45) Date of Patent: Nov. 3, 2020

(54) METHOD AND APPARATUS FOR PRODUCING SEQUENCE VERIFIED DNA

(71) Applicant: GENSINTA, INC., Vilnius (LT)

(72) Inventors: Austen Heinz, San Francisco, CA (US); Anselm Levskaya, San Francisco, CA (US); John T. Mulligan, Seattle, WA (US)

(73) Assignee: GENSINTA, INC., Vilnius (LT)

( * ) Notice: Subject to any disclaimer, the term of this patent is extended or adjusted under 35 U.S.C. 154(b) by 419 days.

(21) Appl. No.: 14/268,832

(22) Filed: May 2, 2014

(65) Prior Publication Data
US 2015/0072873 A1   Mar. 12, 2015

Related U.S. Application Data

(60) Provisional application No. 61/819,211, filed on May 3, 2013.

(51) Int. Cl.
| C12N 15/10 | (2006.01) |
| C40B 20/08 | (2006.01) |
| C40B 50/14 | (2006.01) |

(52) U.S. Cl.
CPC .......... *C12N 15/1065* (2013.01); *C40B 20/08* (2013.01); *C40B 50/14* (2013.01);
(Continued)

(58) Field of Classification Search
None
See application file for complete search history.

(56) References Cited

U.S. PATENT DOCUMENTS

| 2010/0216648 A1 | 8/2010 | Staehler et al. |
| 2012/0283110 A1 | 11/2012 | Shendure et al. |
| 2014/0155297 A1 | 6/2014 | Heinz |

FOREIGN PATENT DOCUMENTS

WO   WO 2014/179735 A1   11/2014

OTHER PUBLICATIONS

Notification of Transmittal of the International Search Report and the Written Opinion of the International Searching Authority, or the Declaration and International Search Report and Written Opinion of the International Searching Authority for International Application No. PCT/US2014/036645 dated Sep. 25, 2014, 11 pages.

*Primary Examiner* — Kaijiang Zhang
(74) *Attorney, Agent, or Firm* — Moser Taboada

(57) ABSTRACT

A method of retrieving a subset of polynucleotide molecules from a mixture of polynucleotide molecules includes receiving a mixture of nucleotide sequences comprising one or more polynucleotide molecules, synthesizing one or more identifier (ID) regions onto the one or more polynucleotide molecules, and sequencing members of the population of polynucleotide molecules to associate the sequence of one or more of the molecules (the "Polynucleotide Sequence") with the sequence of the attached ID region (the "ID Sequence"). The method also includes generating a bead-bound library of one or more beads comprising subsets of identical polynucleotide molecules. Each bead is identified by the ID Sequence of the associated Polynucleotide Sequence. The method further includes sequencing the one or more ID regions of each bead to generate ID Sequence information for each bead, combining the Polynucleotide Sequence information, the one or more ID Sequences, and coordinates of each bead to identify the Polynucleotide Sequence on the bead, and retrieving the bead with its associated Polynucleotide Sequence from the flow cell based on the absolute coordinate position of the bead.

16 Claims, 16 Drawing Sheets

(52) U.S. Cl.
CPC ............... *B01J 2219/005* (2013.01); *B01J 2219/00572* (2013.01); *B01J 2219/00596* (2013.01)

METHOD AND APPARATUS FOR PRODUCING SEQUENCE VERIFIED DNA

CROSS-REFERENCES TO RELATED APPLICATIONS

This application claims priority to U.S. Provisional Patent Application No. 61/819,211, filed on May 3, 2013, entitled "Method and Apparatus for Producing Sequence Verified DNA," the disclosure of which is hereby incorporated by reference in its entirety for all purposes.

BACKGROUND OF THE INVENTION

Synthetic nucleic acids (e.g., synthetic DNA) have applications in molecular biology and biomedical research and development. The synthesis of synthetic nucleic acids is typically performed using column-based synthesizers.

The applications for synthetic nucleic acid polymers include use as primers for the polymerase chain reaction (PCR) and sequencing of DNA. Despite the progress made in the synthesis and recovery of synthetic DNA, there is a need in the art for improved methods related to DNA synthesis and recovery.

Current strategies for gene synthesis involve the bulk-scale synthesis of individual oligonucleotides using column-based phosphoramidite synthesis followed by enzymatic assembly, cloning into bacteria, and individual sequence verification. However, these strategies commonly involve unsuccessful syntheses and may necessitate a costly repeat of the entire process resulting in a labor-intensive, expensive, and low-throughput process.

SUMMARY OF THE INVENTION

The present invention relates to the field of artificial DNA synthesis, DNA sequencing, and on a broader level, the recently established field of synthetic biology. Embodiments of the present invention can be used for the fabrication of genes, gene circuits, small mitochondrial chromosomes, large bacterial chromosomes, and the like. In particular, embodiments are relevant to whole genome modification such as codon optimization or alternate codon schemes for artificial amino acids or any other project related to large scale rewriting.

According to a specific embodiment of the present invention, a method of retrieving a subset of polynucleotide molecules from a mixture of polynucleotide molecules is provided. The method includes receiving a mixture of nucleotide sequences comprising one or more polynucleotide molecules and synthesizing one or more identifier (ID) regions onto the polynucleotide molecules. The method then includes amplifying the members of the population of polynucleotide molecules to create multiple copies of each molecule and sequencing a subset of the amplified molecules to associate the sequence of one or more of the molecules (the "Polynucleotide Sequence") with the sequence of the attached ID region (the "ID Sequence"). The method further includes generating a bead-bound library of one or more beads comprising subsets of identical polynucleotide molecules, wherein each bead is identified by the ID Sequence of the associated Polynucleotide Sequence, sequencing the one or more ID regions of each bead to generate ID Sequence information for each bead. The method further includes combining the Polynucleotide Sequence information, the one or more ID Sequences, and coordinates of each bead to identify a Polynucleotide Sequence on the bead, and retrieving the bead with its associated bead ID and variable sequence from the flow cell based on the absolute coordinate position of the bead.

According to an embodiment of the present invention, a method of retrieving a subset of polynucleotide molecules from a mixture of polynucleotide molecules is provided. The method includes receiving a mixture of nucleotide sequences comprising one or more polynucleotide molecules and synthesizing one or more identifier (ID) regions onto the polynucleotide molecules. The method then includes cloning the polynucleotide molecules to derive one or more subsets of identical polynucleotide molecules and generating a bead-bound library of the beads comprising the subsets of identical polynucleotide molecules, wherein each bead is identified by an associated bead ID. The method further includes sequencing the bead ID of each bead multiple times to generate sequence information for each bead and combining the sequence information, the bead ID and the coordinates of each bead to identify a variable sequence on the bead. The method then includes determining the absolute coordinate position of the bead on a flow cell by comparing the variable sequence on the bead with a list of sequenced bead IDs in the bead-bound library and retrieving the bead with its associated bead ID and variable sequence from the flow cell based on the absolute coordinate position of the bead.

According to a specific embodiment of the present invention, a method of retrieving a subset of polynucleotide molecules from a mixture of polynucleotide molecules is provided. The method includes receiving a mixture of nucleotide sequences comprising one or more polynucleotide molecules and synthesizing one or more identifier (ID) regions onto the polynucleotide molecules. The method then includes generating a library of beads comprising a bead-bound population of identical polynucleotide molecules generated by clonal amplification of a single polynucleotide molecule per bead, wherein each bead is identified by an associated bead ID. The method further includes sequencing the bead ID regions of each bead. The method further includes the release of a portion of the bead-bound polynucleotide molecules from each of a plurality of the members of the bead library and sequencing members of this population of polynucleotide molecules to associate the Polynucleotide Sequence of the one or more of the polynucleotide molecules with the ID Sequence of the one or more bead ID regions; and combining the Polynucleotide Sequence information, the ID Sequence information and the coordinates of each bead to identify a Polynucleotide Sequence on a plurality of the beads. The method then includes determining the absolute coordinate position of the bead on a flow cell by comparing the Polynucleotide Sequence on the bead with a list of sequenced bead IDs in the bead-bound library and retrieving the bead with its associated bead ID and variable sequence from the flow cell based on the absolute coordinate position of the bead.

According to another specific embodiment of the present invention, a method of retrieving a subset of polynucleotide molecules from a mixture of polynucleotide molecules is provided. The method includes receiving a mixture of nucleotide sequences comprising one or more polynucleotide molecules, synthesizing one or more identifier (ID) regions onto the one or more polynucleotide molecules, and cloning the one or more polynucleotide molecules to derive one or more subsets of identical polynucleotide molecules by generating a bead-bound library of one or more beads comprising the one or more subsets of identical polynucleotide molecules. Each bead is identified by an associated bead ID and is positioned at a predetermined position. The method also includes sequencing the one or more ID regions of each bead to generate sequence information for each bead, releasing a portion of the bead-bound polynucleotide molecules from each of a plurality of the members of the bead library and sequencing members of this population of polynucleotide molecules to associate the sequence of the one or more of the polynucleotide molecules (the "Polynucleotide Sequence") with the sequence of the one or more ID regions (the "ID Sequence"), and combining the sequence information, the one or more ID regions, and coordinates of each bead to identify a variable sequence on the bead. The method further includes determining an absolute coordinate position of the bead on a flow cell by comparing the variable sequence on the bead with a list of sequenced bead IDs in the bead-bound library and retrieving the bead with its associated bead ID and variable sequence from the flow cell based on the absolute coordinate position of the bead.

According to another embodiment of the present invention, a method of retrieving a subset of polynucleotide molecules from a mixture of polynucleotide molecules is provided. The method includes receiving a mixture of nucleotide sequences comprising one or more polynucleotide molecules, synthesizing one or more identifier (ID) regions onto the one or more polynucleotide molecules, and sequencing members of the population of polynucleotide molecules to associate the sequence of one or more of the molecules (the "Polynucleotide Sequence") with the sequence of the attached ID region (the "ID Sequence"). The method also includes generating a bead-bound library of one or more beads comprising subsets of identical polynucleotide molecules. Each bead is identified by the ID Sequence of the associated Polynucleotide Sequence. The method further includes sequencing the one or more ID regions of each bead to generate ID Sequence information for each bead, combining the Polynucleotide Sequence information, the one or more ID Sequences, and coordinates of each bead to identify the Polynucleotide Sequence on the bead, and retrieving the bead with its associated Polynucleotide Sequence from the flow cell based on the absolute coordinate position of the bead.

Numerous benefits are achieved by way of the present invention over conventional techniques. For example, embodiments of the present invention provide improved methods and systems for characterizing and recovering synthetic DNA sequences. In an implementation, embodiments of the present invention provide methods for retrieving error-free DNA molecules for use in assembling genes and other DNA sequences. These and other embodiments of the invention along with many of its advantages and features are described in more detail in conjunction with the text below and attached figures.

DETAILED DESCRIPTION OF SPECIFIC EMBODIMENTS

Some embodiments of the present invention disclose techniques for the recovery of correct DNA sequences using targeted laser ejection. In one embodiment, a synthesis by sequencing process is disclosed that utilizes electrode-based or light based DNA oligonucleotide synthesis on massively parallel microarrays. After synthesis, the oligos are released from the microarray and amplified to generate multiple identical copies of each oligonucleotide molecule. In an embodiment of the invention, amplification occurs on a bead and a portion of the amplified molecules are released from the bead and sequenced on a second sequencing platform. The ID sequence is determined for one or more beads and the beads carrying error-free sequences are identified by comparing the ID sequence to the full sequence of the molecule generated using the second sequencing method. After capturing the oligos into multiwell plates, larger genes are then assembled using an assembly technique. By utilizing synthesis by sequencing, effective cost reduction in the synthesis of DNA can be achieved. In addition, by sequencing prior to assembly, the disclosed technique enables the accurate selection of sequences for downstream gene assembly. By using a second sequencing method to generate most of the sequence data, the disclosed technique can take advantage of advanced sequencing methods, reducing cost and increasing accuracy. While the typical costs of DNA synthesis using techniques such as column-based phosphoramidite synthesis is typically around $1 to make 14 bp, the disclosed technique enables the production of as many as 16,000 bp using an automated synthesis by sequencing pipeline. Other numbers of base pairs can also be produced. Additionally, because errors are filtered out prior to DNA assembly, the disclosed technique enables combining many more oligos at a time while enabling a high probability of correctly assembled clones, thereby reducing the cost of downstream gene and genome synthesis.

Figure 1:
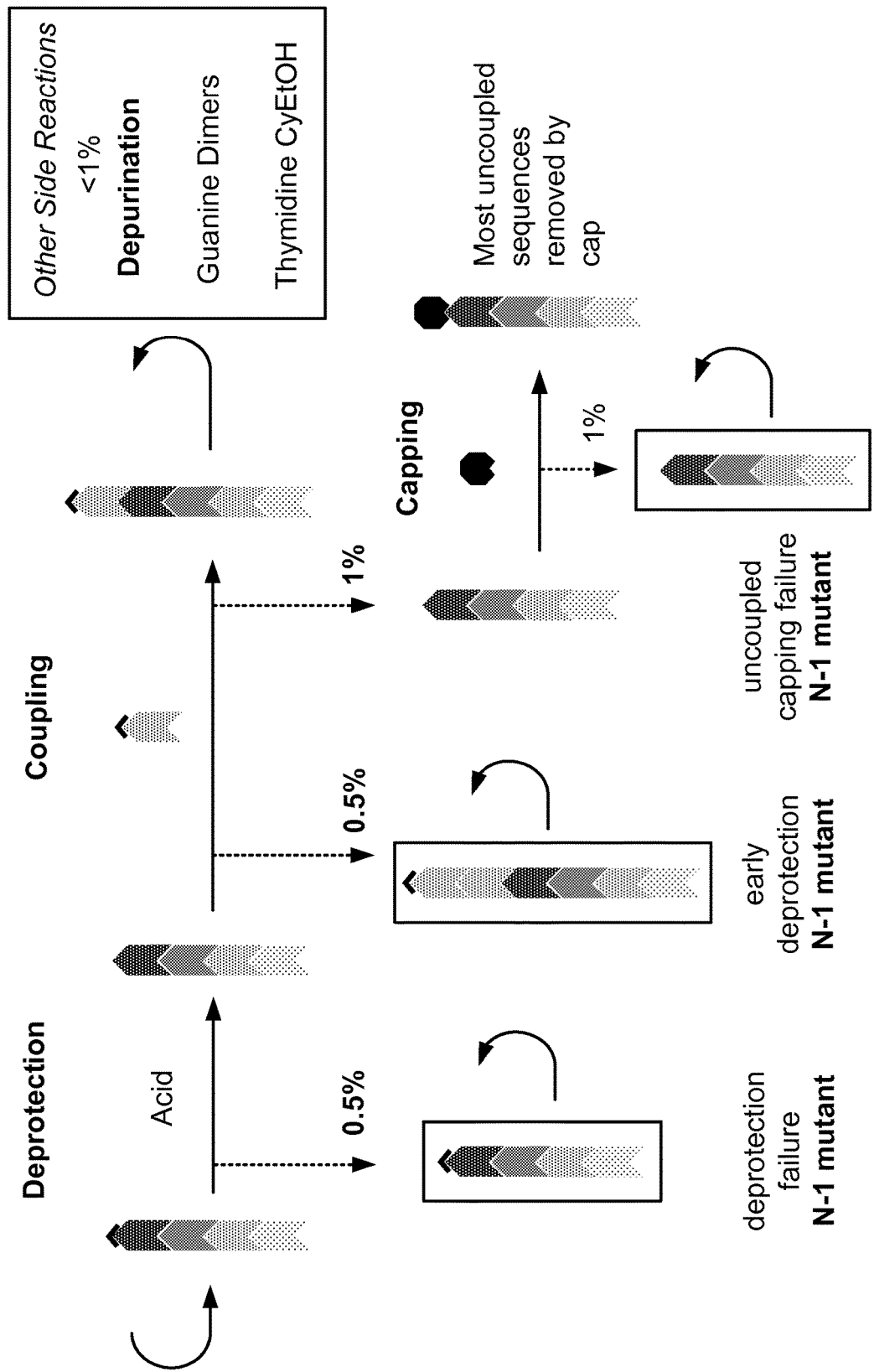
FIG. 1 is a simplified diagram illustrating the side products of a phosphoramidite coupling cycle during a DNA synthesis process.

FIG. 1 is a simplified diagram illustrating the side products of a phosphoramidite coupling cycle during a DNA synthesis process. The chemistry underlying microarray production methods corresponds to phosphoramidite-based chemistry which is used for oligo-synthesis and is generally regarded as being the optimal bulk-synthesis method. Independent of the underlying chemistry deployed, oligonucleotide synthesis is a series of uncatalyzed sequential chemical reactions subject to fundamental statistical limits. Typically, a tradeoff is achieved between: 1) Driving the desired reaction to completion by adding concentrated, strong reactants and increasing the reaction time to reach completion; 2) Minimizing many unwanted side reactions such as Depurination, GG dimer formation, and N3 Thymidine Cyanoethylation, etc. by using gentler reactants and minimizing the reaction time and 3) Maximizing the speed of production and the raw cost of ideal vs. abundant reagents. Commercially available microarray synthesis platforms use conventional phosphoramidite chemistry with error rates of 0.05% per base resulting in 60% of 100 mers and 47% of 150 mers being correct.

High-throughput sequencers have traditionally been used as filtering mechanisms for microarray DNA. However, existing attempts to retrieve sequenced DNA have relied on methods that are typically impractical for industrial use. These methods include mechanical transfer of sequencing beads with pulled-glass pipettes and digital micromirror directed photo-release of sequenced DNA into bulk fluid. In addition, electronic fabrication techniques such as Laser Direct Write, Laser Pressure Catapulting, or Laser Induced Forward Transfer have also been used as a means of transferring micron-sized amounts of material between a 2D source and a receiver substrate. Thin metal films, fluids, polymers, and even living cells have been transferred in a rapid, non-contact fashion by using focused Q-switched laser pulses targeted onto these materials. Modern solid-state Q-switched lasers have been utilized to operate at kilohertz speeds while maintaining millijoule pulse energies, allowing for extremely rapid transfer of material.

Synthesis of large DNA molecules has also been traditionally performed by the assembly of many short oligonucleotide fragments of DNA 60-100 bp in length. Each DNA fragment is synthesized one at a time at an excessive macroscopic scale resulting in a high cost for the DNA synthesis process. Several attempts have been made to drop the cost of these building blocks by building them on microarrays using controlled light or electronics. However, microarray DNA is both error-prone and comes as dilute, extremely complex mixtures of thousands of different species. To effectively use the million building blocks on a large microarray, the DNA fragments need to be sorted from one another and filtered such that only correctly synthesized pieces are used for the final assembly steps.

In one embodiment of the present invention, this is performed by using massively parallel sequencers that sequence copies on beads of single-molecule DNA species sampled from the microarray. By sequencing many more copies than unique species, correct copies of every microarray synthesized species may be identified. In one embodiment, high-speed pulsed lasers are used to eject the correct beads of each sequence into unique, specified combinations in 384-well plates for assembly into genes. Using this approach, cost decreases in the DNA synthesis pipeline may be achieved.

In certain embodiments, the disclosed technology achieves a high-throughput collection and transfer of millions of beads without risking cross-contamination between different sequences at an extremely fast rate. In other embodiments, the disclosed technology uses a dry, non-contact technique as an ultra-fast means of collecting sequencing beads intact into 384 well plates. In one embodiment, laser catapulting is used as a non-contact, non-contaminating, and high-throughput transfer mechanism of sequencing beads.

Figure 2:
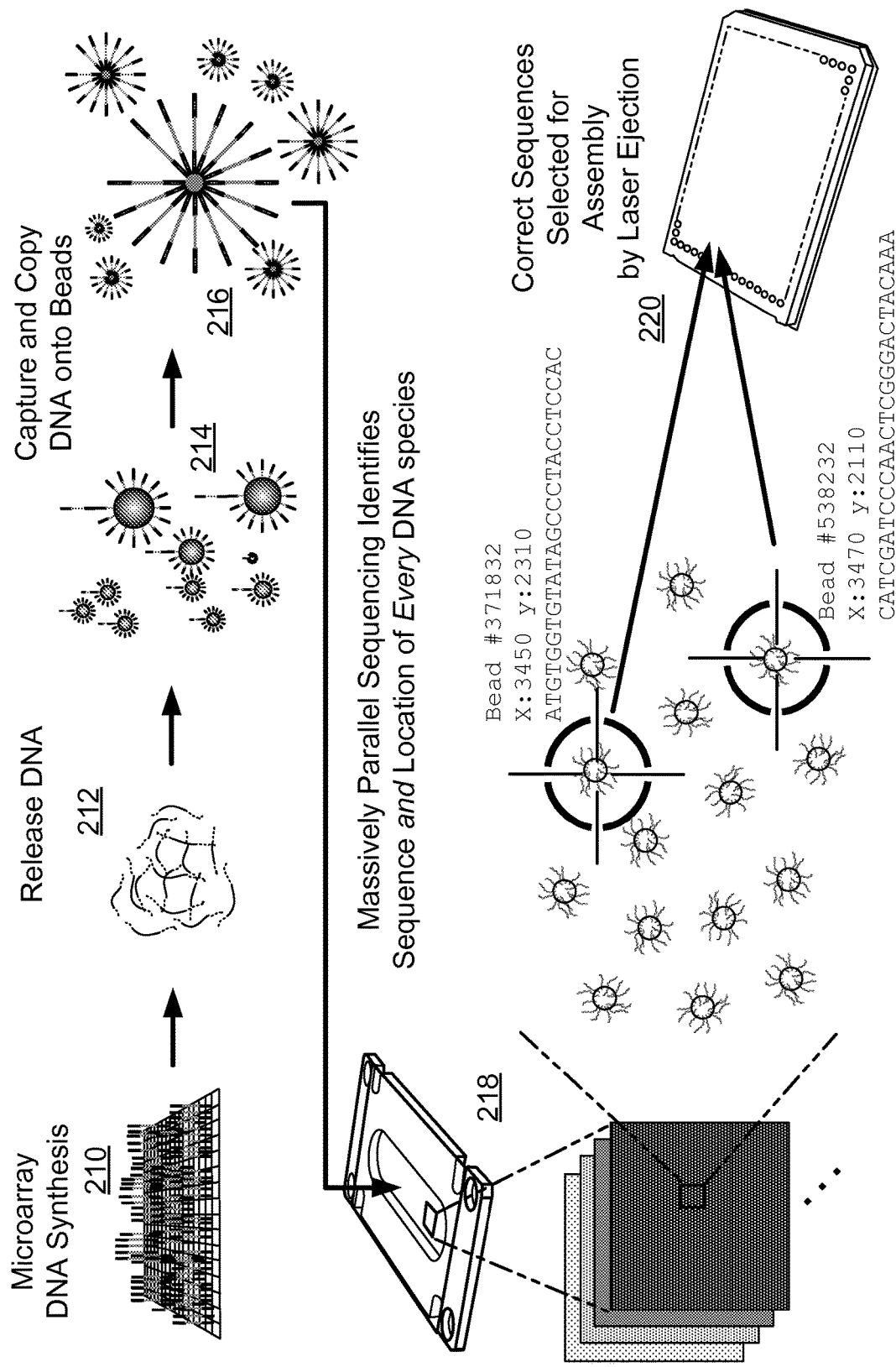
FIG. 2 is a simplified block diagram of a massively parallel sequencing process used for DNA synthesis.

FIG. 2 is a simplified block diagram of a massively parallel sequencing process used for DNA synthesis. In one embodiment, high-throughput sequencing is utilized as a physical method for filtering, sorting and amplifying microarray synthesized oligos for gene synthesis. The massively parallel sequencing process identifies the sequence and location of every DNA molecule. By sequencing prior to assembly, correct sequences from a mixture of correct and incorrect sequences may be identified. Sequencing prior to assembly also physically separates sequences and allows arbitrary subsets of the entire million-species pool to be selected for ejection into a single receiver vessel. This enables the user to determine the number of oligos that are assembled in the downstream assembly. In this manner, more than tens of sequences at a time may be assembled reliably, which is much fewer than the hundreds of thousands of sequences that can be synthesized on a single microarray.

As illustrated in FIG. 2, microarray synthesis of DNA is performed (210). The DNA are released (212) and captured and copied onto beads (214 and 216). As an example, 100,000 to 1,000,000 identical copies can be cloned on each bead. Massively parallel sequencing techniques are used to identify the sequence and location of each bead (218) and then laser ejection is used to eject the desired bead (220) and thus to select the DNA strands of interest.

In one implementation, the ID sequences may be sequenced using a sequencer such as the Roche 454 next-generation pyrosequencer or a polony-based genome sequencer. Using the sequence information to determine the location of the sequencing beads, a focused laser (such as the Continuum Minilite laser) is then used to eject the individual beads and collect them into 96 well plates in one implementation. In a particular embodiment, ejection of the sequencing bead is confirmed by PCR and traditional Sanger resequencing, but this is not required by the present invention. However, pyrosequencing chemistry using a pyrosequencer may not filter out common kinds of deletion errors found in synthesized DNA especially in short homopolymeric runs. In an alternate embodiment, fluorescently-labeled, reversibly-terminated nucleotide chemistry used by traditional sequencing by synthesis strategies may also be utilized as a sequencing method to reliably detect the ID sequences. Additional discussion related to DNA synthesis and selection is provided in U.S. patent application Ser. No. 13/775,745, filed on Feb. 25, 2013, the disclosure of which is hereby incorporated by reference in its entirety for all purposes.

Figure 3A:
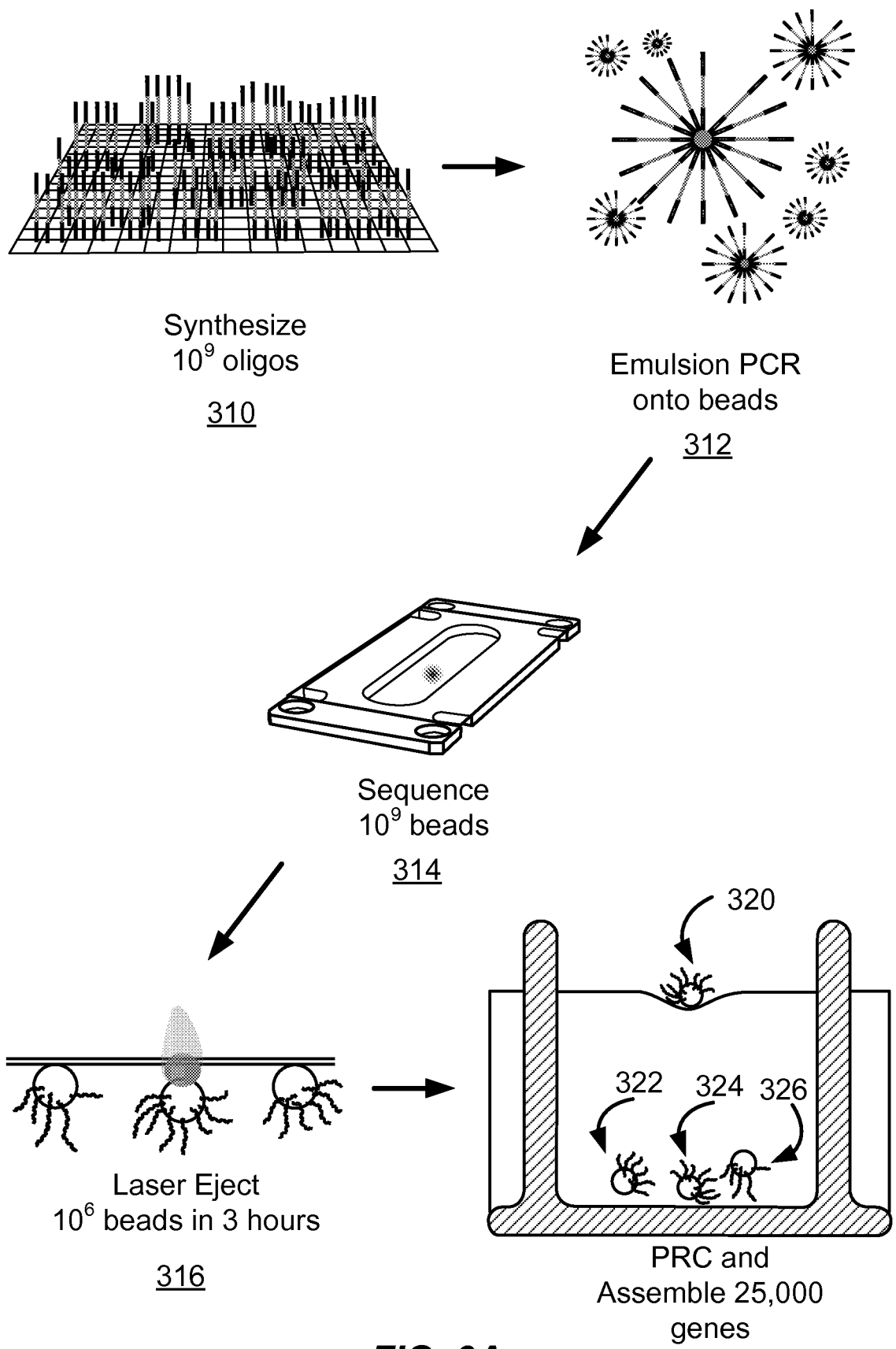
FIG. 3A is a simplified diagram illustrating the synthesis by sequencing process for high-throughput gene assembly, according to one embodiment of the present invention.

FIG. 3A is a simplified diagram illustrating the synthesis by sequencing process for high-throughput gene assembly, according to one embodiment of the present invention. The syntheses of DNA fragments are performed, for example, on a microarray (310). After the microarray synthesis of the DNA fragments is performed, each DNA fragment is attached to a bead (312) and then copied multiple times (e.g., 100,000 times) on the bead (314). In one embodiment, emulsion polymerase chain reaction (PCR) is used to amplify each DNA fragment into multiple copies of the DNA fragment. In addition to the processes illustrated in FIG. 3A, some embodiments use two parallel sequencing methods, one for the whole molecule using any large capacity sequencing method (e.g., Illumina or Oxford Nanopore) as illustrated in FIG. 3A in addition to a second sequencing method using beads as described herein and shown in FIG. 3B. After sequencing, laser ejection is used to eject a subset of the beads (316). In the illustrated embodiment, beads 320, 322, 324, and 326 are ejected into a well of a microfluidic device (shown in cross-section), which can simplify downstream processing. In one implementation, beads 320, 322, 324, and 326 have multiple copies of the same DNA fragment, whereas in other implementations, each of the beads has multiple copies of different stands, for example, the DNA strands that are needed to assemble a given gene. Thus, four different beads are illustrated although this is not required by the present invention.

Figure 3B:
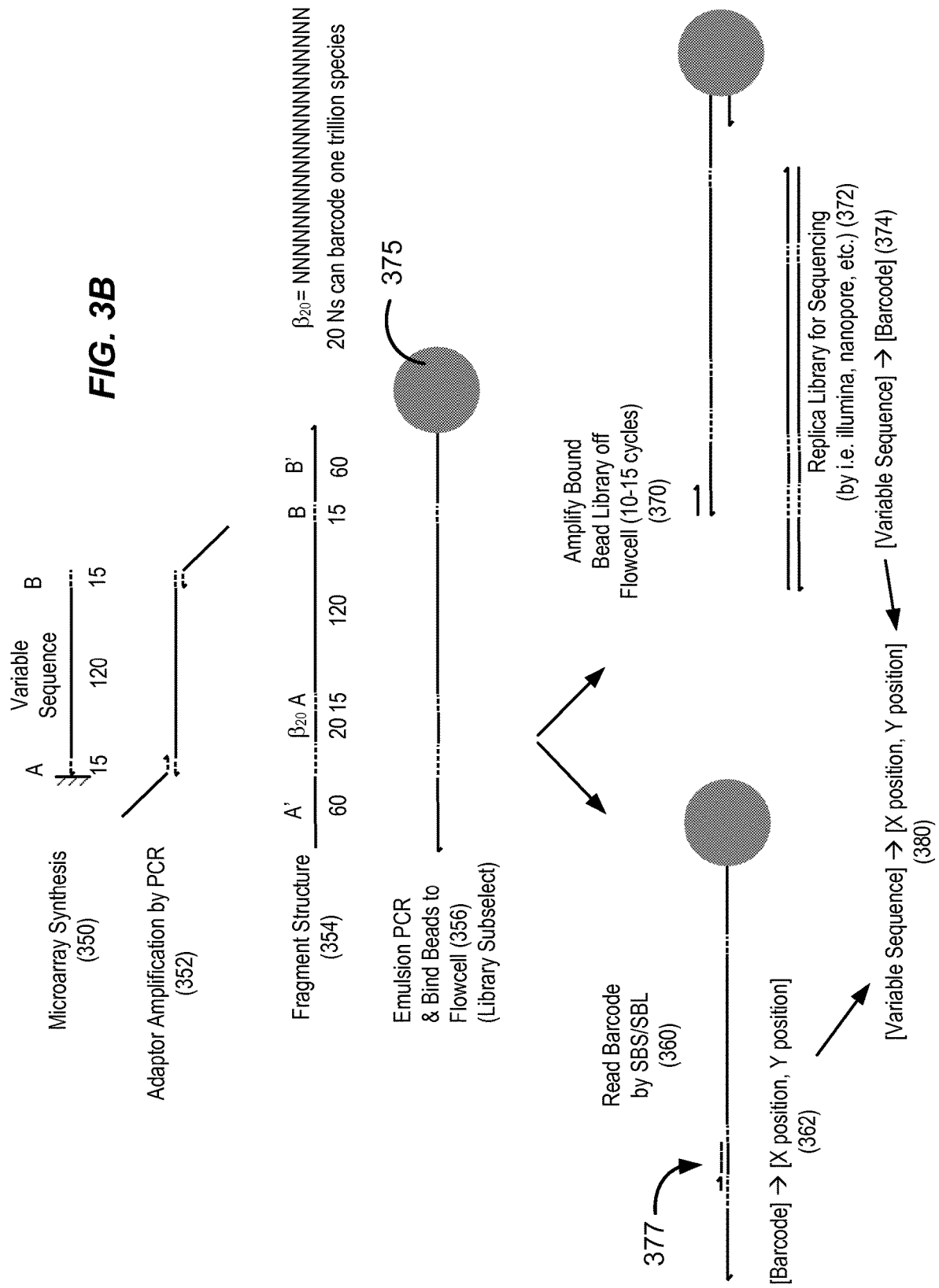
FIG. 3B illustrates a synthesis process for sequencing DNA fragments according to an embodiment of the present invention.

FIG. 3B illustrates a synthesis process for sequencing DNA fragments according to an embodiment of the present invention. A typical structure of the DNA fragment template is illustrated in this figure as well as one round of amplification that occurs before the DNA fragments are attached to beads. As illustrated in FIG. 3B, the DNA fragment structure obtained as a result of amplification includes tailed primers that add a unique identifier or barcoding sequence to each DNA fragment structure. Each DNA fragment is then amplified on a bead to generate a population of DNA fragment copies. In one example, the flowcell typically has 40 million species. In the present specification, the terms "Polynucleotide Sequence" and "variable sequence" are used interchangeably. Additionally, the terms "ID Sequence," "bead ID," and "unique ID" are also used interchangeably.

Initially a variable sequence of interest (also referred to as a payload sequence) is identified, for example, a variable sequence 120 base pairs long and tailed primers are added by microarray synthesis (350). In the illustrated example, a universal A and a universal B, each 15 base pairs long are added to the 120 base pair variable sequence. As will be evident to one of skill in the art, the actual lengths of the variable sequence and the universals will differ depending on the particular DNA sequences of interest and the lengths illustrated herein are not intended to limit the present invention since shorter or longer variable sequences and universals are included within the scope of the present invention. Adaptor amplification by PCR (352) is then performed. In order to later select the variable sequence of interest, one or more unique identifiers, also referred to as a barcode, is added to the variable sequence, which could be a variable sequence that is going to be used to build a gene. As illustrated herein, PCR is utilized to add the unique identifier to the variable sequence. After amplification, beads with the desired variable sequence can be identified and selected using the unique identifier attached to the desired variable sequence as described below.

The fragment structure (354) formed using PCR is illustrated as the variable sequence (120 base pairs), the primers A and B, a unique identifier $\beta_{20}$ and second level universals A' and B', both 60 base pairs long. Each variable sequence of interest thus has a unique identifier attached to it, for example, a random strand of 20 base pairs as illustrated by unique identifier 1320. Although the unique identifier $\beta_{20}$ is illustrated as a single set of 20 nucleotides, this is not required by the present invention as will be explained in additional detail below. 20 base pairs are utilized for the unique identifier as an example, providing on the order of one trillion different unique identifiers, but the length of the unique identifier can be varied as appropriate to the particular application. In an embodiment, the unique identifier $\beta_{20}$ is a random set of base pairs although this is not required. Emulsion PCR is used and the stand is bound to the bead 375.

Embodiments of the present invention can utilize a first sequencer to read the unique identifier, which is a relatively short region, and a second, more advanced and expensive sequencer to read both the unique identifier and the payload sequence of the fragment. Correlation between the sequencers is provided by the unique identifier, which is read by both sequencers.

Referring to FIG. 3B, the process splits into two flows. The first flow (360, 362), reads the unique identifier or barcode using a first sequencer, which can be an inexpensive sequencer since only the relatively short (e.g., 20-30 base pair) region of the unique identifier is sequenced. As illustrated, a portion of the amplified DNA fragments is then released from the beads and sequenced using the first sequencing platform. The unique identifier or barcode 377 can be read by DNA sequencing technologies such as Sequencing By Synthesis (SBS) or Sequencing by Ligation (SBL) (360) although other sequencing chemistries can be used. During sequencing by the first sequencer, the unique identifier [Barcode] and the position of the bead being read [X position, Y position] is tracked so that the barcode sequence then enables the identification of the desired bead species for ejection (362). In one embodiment, the absolute coordinates of the beads obtained by the DNA sequencing plate (i.e., first sequencer) are mapped to the coordinate system of a laser ejection system in order to accurately target each bead with the laser. The lasers then eject the correct beads of each sequence into unique, specified combinations in a container (e.g., 384-well plates) for assembly into genes as described more fully below.

During amplification, there are going to be multiple samples of a specific target variable sequence. Some of the samples will be synthesized correctly and some of the samples will be synthesized incorrectly. Thus, there will be multiple beads that are derived from the same target variable sequence, but with different variable sequences. Since each bead includes a unique identifier, the beads that include the correctly synthesized target variable sequence can be identified.

In the second flow (370, 372, 374) the bound bead library is amplified off of the flowcell (370) using a second (e.g., commercial) sequencer. The flowcell-bound library is then replicated by low-cycle PCR for direct next-gen sequencing (372). Using the sequence read using the second sequencer, which reads the fragment structure including the variable sequence and the unique identifier, the variable sequence that is desired can be correlated to the unique identifier (374). Given the correlation between the variable sequence and the barcode (374, [Variable Sequence]→[Barcode]) and the correlation between the barcode and the (X,Y) position of the bead to the barcode (362, [Barcode]→[X position, Y position]), it is possible to determine the (X,Y) position of the variable sequence of interest (380, [Variable Sequence]→[X position, Y position]). Subsequently, the desired bead species is ejected for use. In some embodiments, sequencing is performed by the first and second sequencers concurrently or simultaneously, although this is not required by embodiments of the present invention.

In another embodiment, the DNA synthesis process may include sorting and filtering a mixture of synthetic oligonucleotides (which can be referred to as "oligos") that comes from the imperfect synthesis of a specified set of oligos. For example, assume that a specified set of oligos includes 100,000 oligos that include 100,000 text strings of length 100. Each string specifies a unique 'type' of DNA to be made. The synthesis process of such a complicated mixture of synthetic oligonucleotides may typically result in a percentage (say, for example, about 25%) of the molecules of each type being correct. In one embodiment, a process is disclosed that identifies the percentage of correct molecules from a specified set of oligos in a fast, high-throughput batch process using sequencing methods and laser selection of micron-sized beads.

Figure 4A:
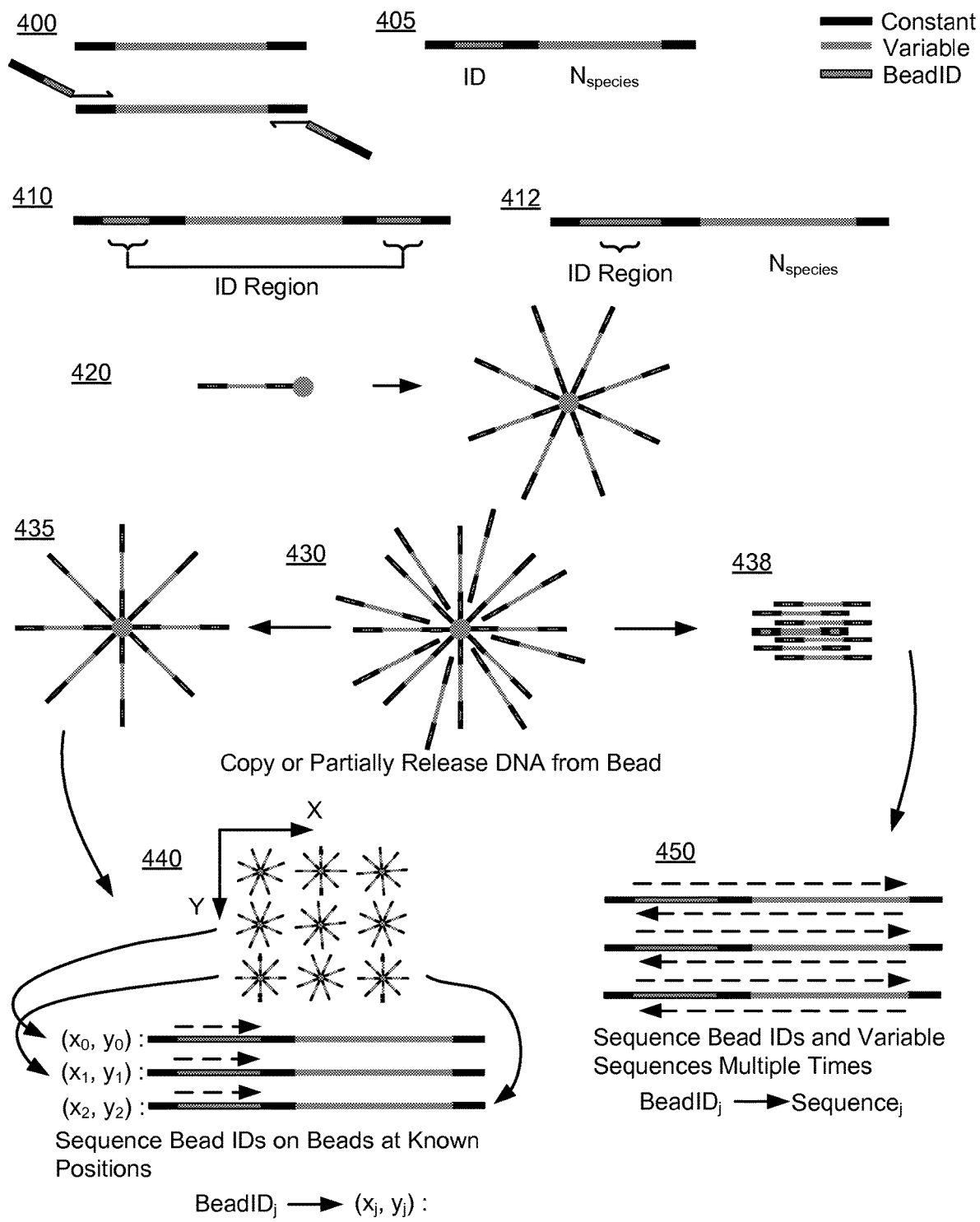
FIG. 4A illustrates a process for isolating a specific subset of polynucleotide molecules from a mixture of polynucleotide molecules, according to one embodiment of the present invention.

FIG. 4A illustrates a process for isolating a specific subset of polynucleotide molecules from a mixture of polynucleotide molecules, according to one embodiment of the present invention. The process illustrated in FIG. 4A shares similarities with the process illustrated in FIG. 3B and description provided in relation to FIG. 3B is applicable to FIG. 4A as appropriate. A mixture of nucleotide sequences (400) having a variable sequence ($N_{species}$) is initially received. Flanking regions are then added to all members of the mixture by using PCR with synthetic oligonucleotides, wherein the flanking regions include a region of randomly incorporated nucleotides (ID). In one embodiment, the randomized regions may be synthesized by adding an equal 1:1:1:1 mixture of 'A', 'C', 'T', 'G' nucleotides during synthesis. In one example, the randomized regions (i.e., the random-nucleotide chain) may occur in a single contiguous sequence on a derived molecule 412. In another example, the randomized regions may be separated into several non-contiguous regions spread throughout the 5'- and 3'-ends of a derived molecule 410. Alternatively, for synthesized mixtures, the randomized regions may also be synthesized directly on each derived molecule, 405 and 412. In one embodiment, the randomized region thus synthesized is referred to as an "Identifier (ID) Region," a unique identifier (ID), or a barcode.

From this mixture of ID Region bearing molecules, single molecules 420 are then sampled randomly from the entire pool and cloned using PCR on beads inside an emulsion. In other embodiments other cloning strategies may also be utilized such as bridge-PCR, or rolony generation.) Accordingly, each bead or 'clone' includes a subset of identical molecules derived from a single molecule in the original pool. Each clone is typically statistically likely to have a unique ID, owing to the combinatorial diversity of the ID string region.

This oversampled library of clones on beads generated as discussed above is then duplicated into an equivalent library freely floating in solution. In one embodiment, this equivalent mixture of nucleotides may be made by copying the sequences on all beads by PCR. In an alternate embodiment, this equivalent mixture of nucleotides may be made by chemically or enzymatically releasing a subset of the molecules bound to each of the beads, 430. The result of this process generates two copies of the same sample from the original ID-bearing polynucleotide library. The first copy is covalently bound to beads, 435 and the second copy is composed of freely suspended nucleotides, 438. These two copies of the "ID-tagged" library are then physically separated by centrifugation or magnetic separation.

The bead-bound library is then adsorbed onto a flowcell. The beads are stuck at particular positions on the flowcell, either randomly or in a regular pattern defined by a photolithographically produced grid of wells, 440. The "ID region" of the molecules on each bead clone is sequenced once using sequencing techniques such as sequencing by synthesis (SBS) or sequencing by ligation (SBL) using a first sequencer. This links the absolute positional coordinates of each bead with its unique ID.

The soluble library is sequenced on a separate, second sequencer, potentially multiple times, generally using "paired-end" sequencing, 450. This provides a multiple-read consensus read of the sequences that is typically more accurate than a single read would provide. Both the bead ID, as well as the variable sequence region is sequenced. This links the bead ID of each clone with the variable region of each clone.

By combining the two sources of sequence data (which include the variable sequence region and the bead ID) and linking them with the clonally-unique ID, the sequence of the full variable region of each bead-bound clone for later physical selection may be determined.

Figure 4B:
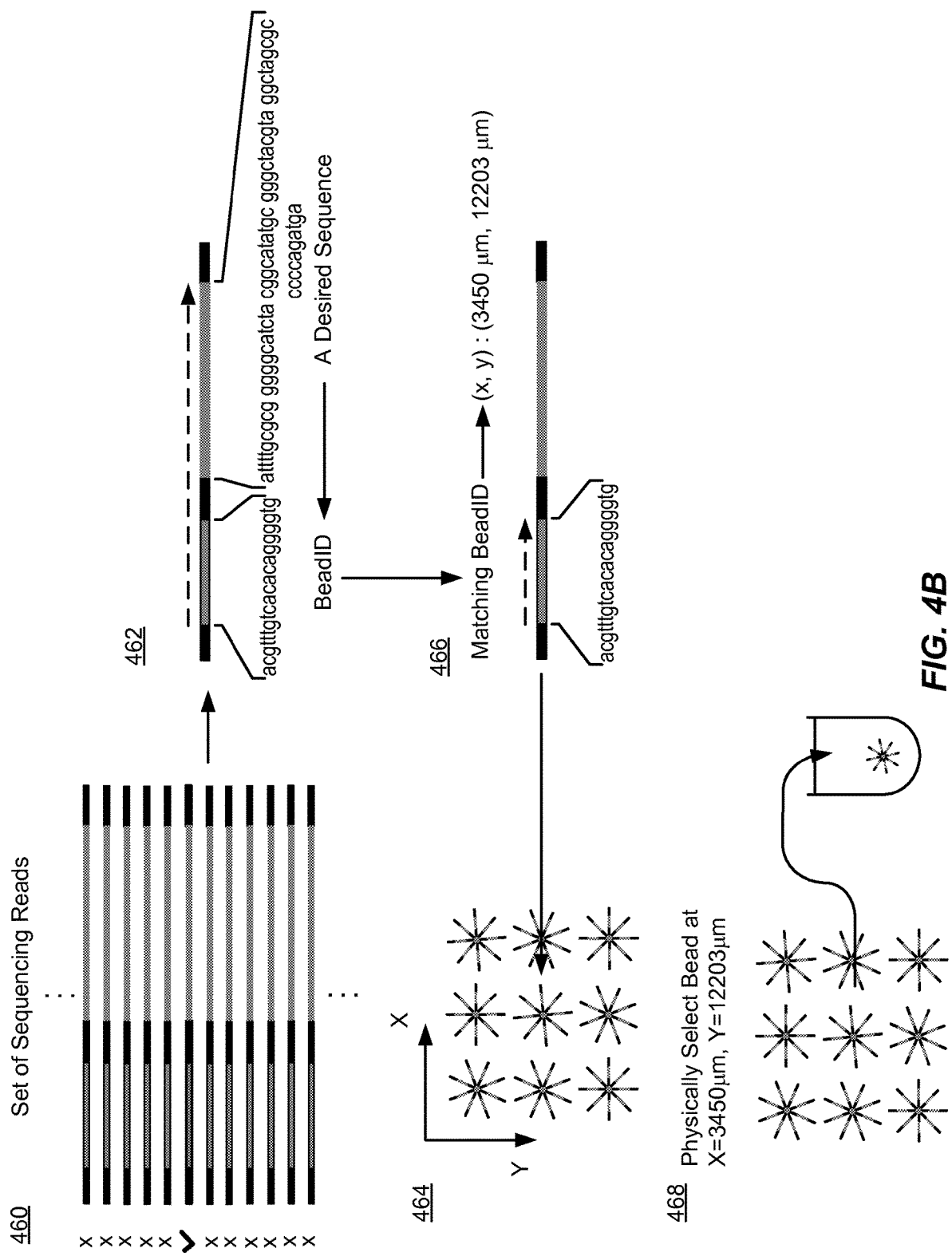
FIG. 4B illustrates a process for determining the absolute position of a bead on a flowcell, according to one embodiment of the present invention.

FIG. 4B illustrates a process for determining the absolute position of a bead on a flowcell, according to one embodiment of the present invention. In one embodiment, this process includes obtaining a list of all read sequences from the soluble pool, 460. For each member of this set that has a desired sequence, a lookup for the ID sequence that was also read from this sample 462, is performed. By comparing this sequence against the list of all sequenced IDs from the bead-bound library, 466, the absolute position of the bead on the flowcell 464, is determined. Based on this position, the bead bearing the known ID and desired sequence is then physically collected from the flowcell using laser-induced forward transfer into a receiving reservoir, 468.

The process for isolating a specific subset of polynucleotide molecules from a mixture of polynucleotide molecule discussed above has several advantages. These advantages include, but are not limited to, optimizing the index sequencer upstream of the laser-ejection for the amount of DNA per clone, the spacing, surface chemistry, and other material aspects associated with laser ejection. Simultaneously, the sequence sequencer may be optimized for read length, fidelity, speed and speed and throughput. Since, the length of the random string is chosen such that the total set of possible random "IDs" is larger by an order of magnitude than the number of clones subsequently picked from the pool, the disclosed process ensures that that there are very few "hash collisions" among the IDs used in the entire set of beads.

Figure 4C:
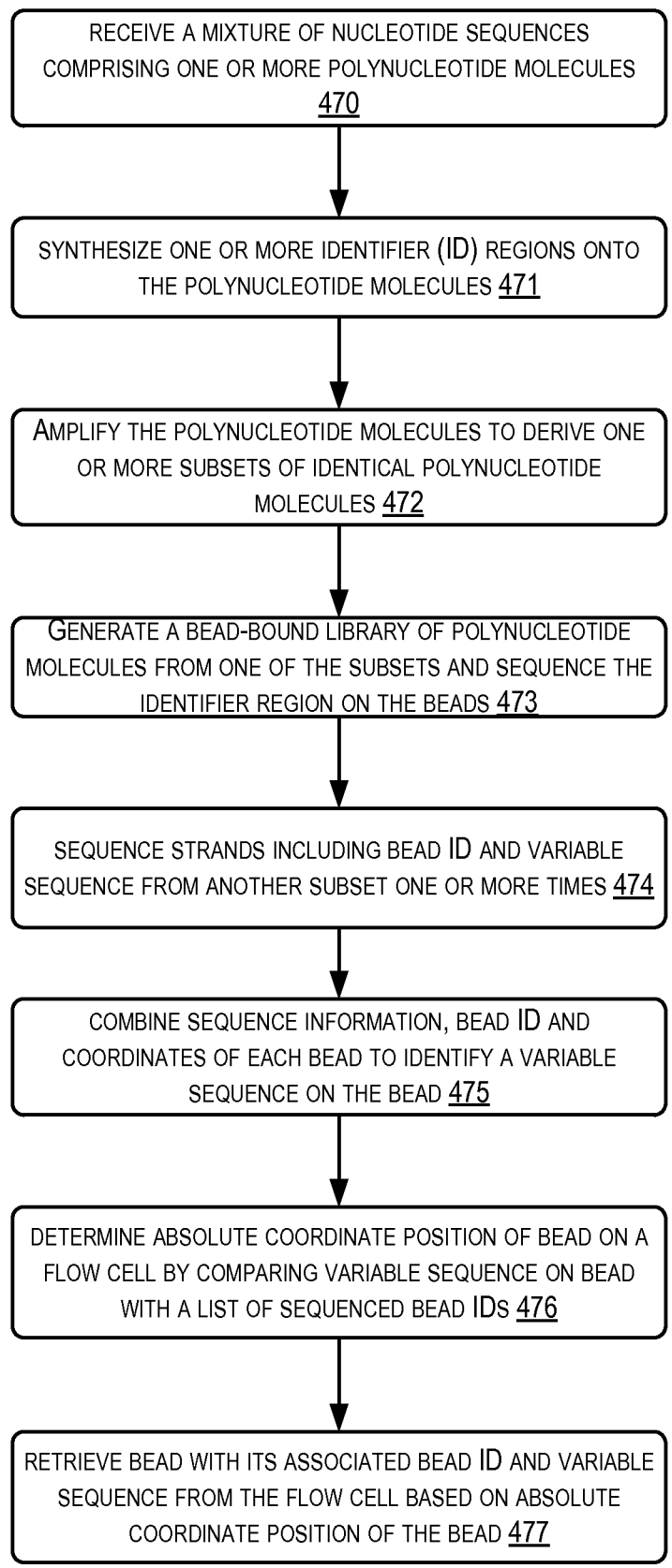
FIG. 4C is a simplified flowchart illustrating a method of isolating a specific subset of polynucleotide molecules from a mixture of polynucleotide molecules, according to one embodiment of the present invention.

FIG. 4C is a simplified flowchart illustrating a method of retrieving a subset of polynucleotide molecules from a mixture of polynucleotide molecules. The mixture of nucleotide sequences is received at 470 including one or more polynucleotide molecules. At 471, one or more identifier (ID) regions are synthesized onto the one or more polynucleotide molecules, wherein the one or more polynucleotide molecules include a variable sequence region. In one embodiment, the ID region includes a region of randomly incorporated nucleotides. As discussed in FIG. 4B, the randomized regions may be synthesized by adding an equal 1:1:1:1 mixture of 'A', 'C', 'T', 'G' nucleotides during synthesis, or may be synthesized directly on each derived molecule.

At 472, the one or more polynucleotide molecules are amplified to derive one or more subsets of identical polynucleotide molecules, wherein the one or more subsets of identical polynucleotide molecules (clones) are bound to one or more beads.

At 473, a bead-bound library of the one or more beads comprising the one or more subsets of identical polynucleotide molecules is generated using a first sequencer, wherein each bead in the bead-bound library is identified by a unique bead identifier (ID). The bead-bound library is adsorbed onto a flowcell, wherein the absolute positional coordinates of each bead in the bead-bound library is linked to its unique bead ID. In one embodiment, and as discussed in FIG. 4A, the beads are stuck at particular positions on the flowcell, either randomly or in a regular pattern defined by a photolithographically produced grid of wells, 450.

At 474, the bead ID and the variable sequence of strands from each bead are sequenced one or more times to generate sequence information. This sequencing is performed on a second sequencer. In one embodiment, both the bead ID, as well as the variable sequence region of each bead is sequenced multiple times. This links the bead ID of each clone with the variable region of each clone (subsets of identical polynucleotide molecules).

At 475, the sequence information including the variable sequence and the bead ID along with the coordinates of each uniquely identified bead are combined to identify the desired variable sequence. At 476, the absolute coordinate position of the bead on the flowcell is determined by comparing the variable sequence on the bead with a list of sequenced bead IDs in the bead-bound library. As discussed in FIG. 4B, this involves performing a lookup for each member of the list of sequenced bead IDs that has the desired variable sequence.

At 477, based on the absolute coordinate position of the bead, the bead with its associated bead ID and variable sequence is physically retrieved from the flow cell.

It should be appreciated that the specific steps illustrated in FIG. 4C provide a particular method of retrieving a subset of polynucleotide molecules from a mixture of polynucleotide molecules according to an embodiment of the present invention. Other sequences of steps may also be performed according to alternative embodiments. For example, alternative embodiments of the present invention may perform the steps outlined above in a different order. Moreover, the individual steps illustrated in FIG. 4C may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 11:
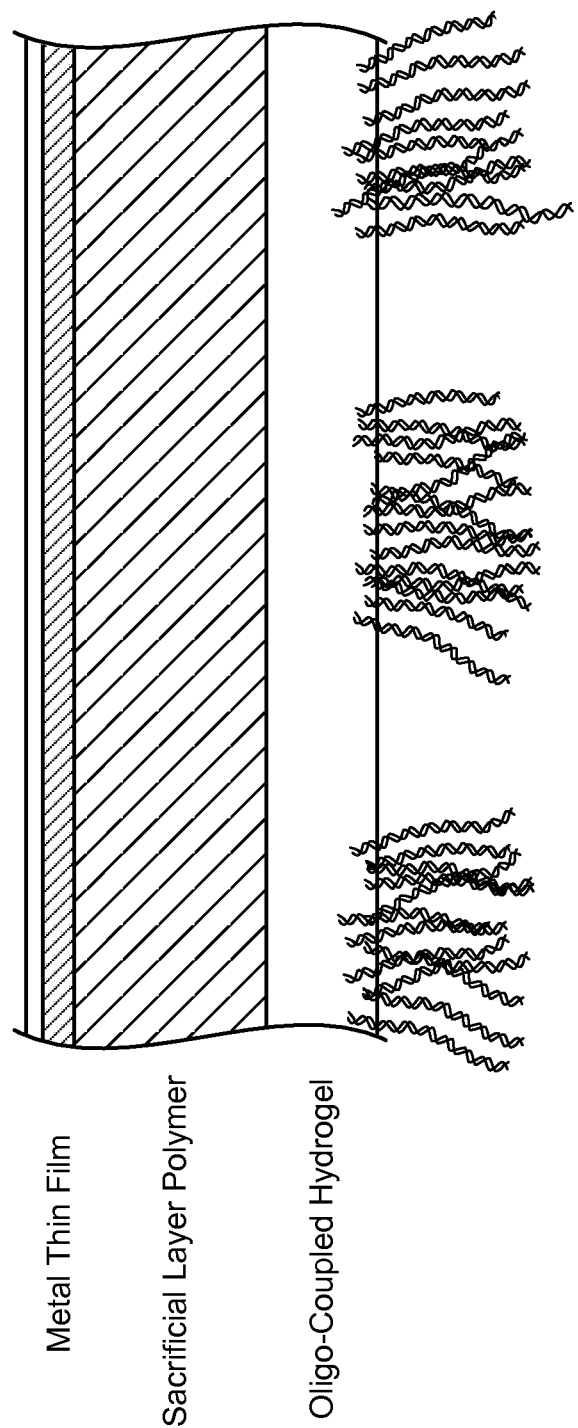
FIG. 11 is a simplified diagram illustrating a metal thin film, sacrificial layer polymer and an oligo-coupled hydrogel.

It should be noted that although FIG. 4C illustrates sequencing in terms of beads, the present invention is not limited to this particular sequencing technique. Other embodiments 2-D clusters or rolonys as illustrated in FIG. 11 can be utilized. While embodiments of the present invention have been illustrated with specific implementations using beads, it will be apparent to one skilled in the art that the invention could be practiced using other methods to physically isolate and amplify individual polynucleotide molecules. As examples, another specific embodiment achieves the isolation and amplification of polynucleotide molecules by solid phase polymerase chain reaction to create spatially separated solid-phase-linked identical populations of polynucleotide molecules inside a gel or on a solid surface. In yet another specific embodiment, the isolation and amplification of polynucleotide molecules is achieved by rolling circle polymerase chain reaction to create spatially separated concatameric polynucleotide particles on a surface. One of ordinary skill in the art would recognize many variations, modifications, and alternatives.

Figure 4D:
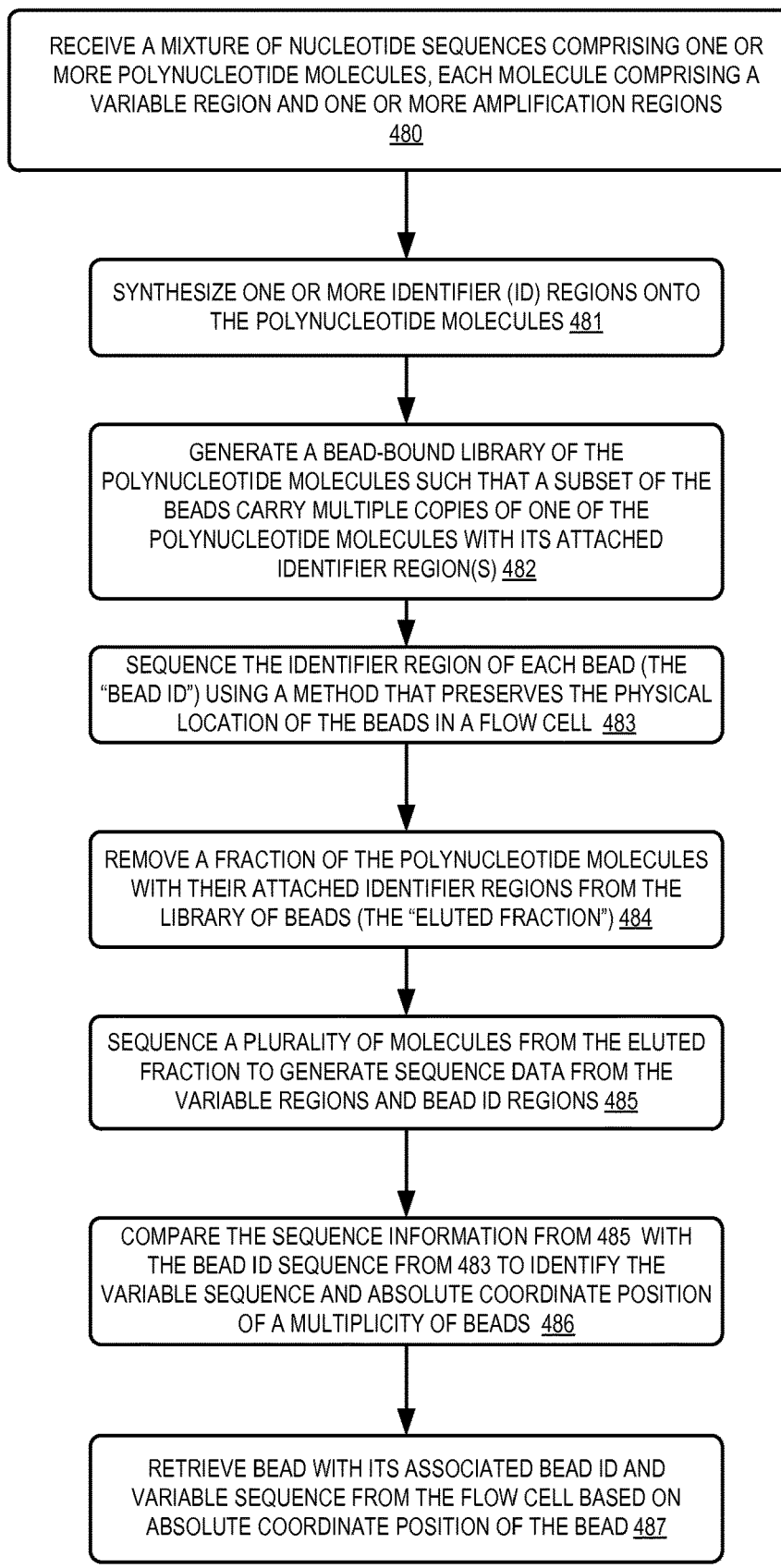
FIG. 4D is a simplified flowchart illustrating a method of selecting a bead having a desired variable sequence according to an embodiment of the present invention.

FIG. 4D is a simplified flowchart illustrating a method of selecting a bead having a desired variable sequence according to an embodiment of the present invention. The method includes receiving a mixture of nucleotide sequences comprising one or more polynucleotide molecules, each molecule comprising a variable region and one or more amplification regions (480). The method also includes synthesizing one or more identifier (ID) regions onto the polynucleotide molecules (481). In some embodiments, the ID region is a random set of base pairs (e.g., 10-30 base pairs). The method includes generating a bead-bound library of the polynucleotide molecules such that a subset of the beads carry multiple copies of one of the polynucleotide molecules with its attached identifier region(s) (482). The method also includes sequencing the identifier region of each bead (the "bead ID") using a method that preserves the physical location of the beads in a flow cell (483).

The method further includes removing a fraction of the polynucleotide molecules with their attached identifier regions from the library of beads (the "eluted fraction") (484). The method includes sequencing a plurality of molecules from the eluted fraction to generate sequence data from the variable regions and bead ID regions (485) and comparing the sequence information from 485 with the bead ID sequence from 483 to identify the variable sequence and absolute coordinate position of a multiplicity of beads (486). The method further includes retrieving the bead with its associated bead ID and variable sequence from the flow cell based on absolute coordinate position of the bead (487). It should be noted that in FIG. 4D, the process illustrated in relation to step 483 could occur before or after the process illustrated in relation to step 484.

It should be appreciated that the specific steps illustrated in FIG. 4D provide a particular method of selecting a bead having a desired variable sequence according to an embodiment of the present invention. Other sequences of steps may also be performed according to alternative embodiments. For example, alternative embodiments of the present invention may perform the steps outlined above in a different order. Moreover, the individual steps illustrated in FIG. 4D may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 4E:
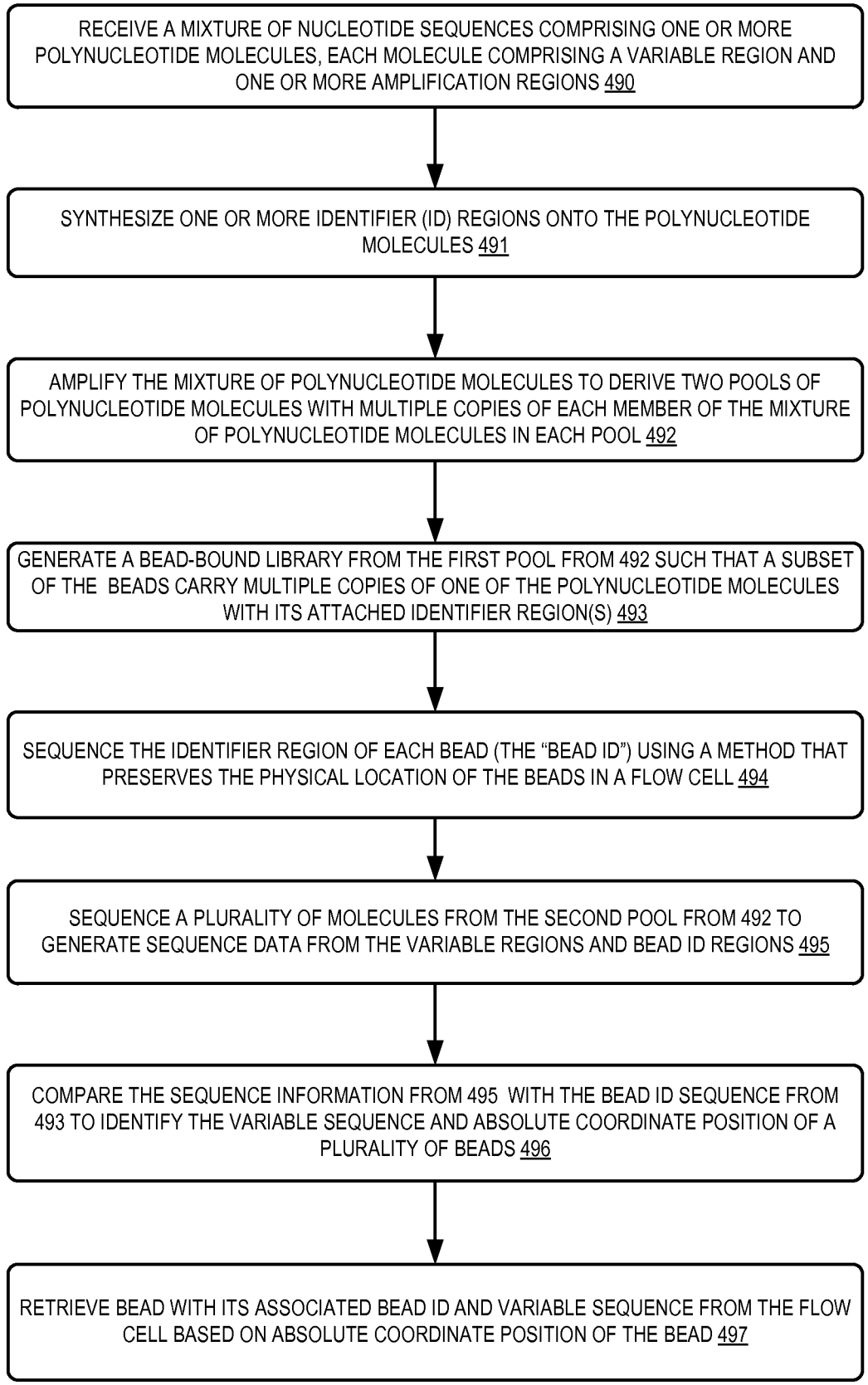
FIG. 4E is a simplified flowchart illustrating a method of selecting a bead having a desired variable sequence according to another embodiment of the present invention.

FIG. 4E is a simplified flowchart illustrating a method of selecting a bead having a desired variable sequence according to another embodiment of the present invention. The method includes receiving a mixture of nucleotide sequences comprising one or more polynucleotide molecules, each molecule comprising a variable region and one or more amplification regions (490) and synthesizing one or more identifier (ID) regions onto the polynucleotide molecules (491). The method also includes amplifying the mixture of polynucleotide molecules to derive two pools of polynucleotide molecules with multiple copies of each member of the mixture of polynucleotide molecules in each pool (492). The method further includes generating a bead-bound library from the first pool from 492 such that a subset of the beads carry multiple copies of one of the polynucleotide molecules with its attached identifier region(s) (493).

The method includes sequencing the identifier region of each bead (the "bead ID") using a method that preserves the physical location of the beads in a flow cell (494) and sequencing a plurality of molecules from the second pool from 492 to generate sequence data from the variable regions and bead ID regions (495). The method also includes comparing the sequence information from 495 with the bead ID sequence from 493 to identify the variable sequence and absolute coordinate position of a plurality of beads (496) and retrieving the bead with its associated bead ID and variable sequence from the flow cell based on absolute coordinate position of the bead (497).

It should be appreciated that the specific steps illustrated in FIG. 4E provide a particular method of selecting a bead having a desired variable sequence according to another embodiment of the present invention. Other sequences of steps may also be performed according to alternative embodiments. For example, alternative embodiments of the present invention may perform the steps outlined above in a different order. Moreover, the individual steps illustrated in FIG. 4E may include multiple sub-steps that may be performed in various sequences as appropriate to the individual step. Furthermore, additional steps may be added or removed depending on the particular applications. One of ordinary skill in the art would recognize many variations, modifications, and alternatives.

Design of a Modular Flow Cell for High-Throughput Sequencing and Laser Ejection

In one embodiment, a sequencing flowcell and a laser ejection system are developed for the recovery of sequencing beads into a macroscopic 384-well format. In some embodiments, the flowcells are designed by dismantling the flowcells in halves for ejection of sequence-bearing beads into collection wells. In addition to designing a well-sealed flow chamber, in certain embodiments a technique is developed for co-registering the absolute coordinate system used by the sequencer and laser ejection system. In one embodiment, a technique of absolute registration or fiducial marking includes mapping the absolute coordinates of the beads obtained by the sequencer to the coordinate system of the laser ejection system in order to accurately target each bead with a pulsed laser. Additionally, an appropriate sacrificial layer is developed that comprises a thin-deposition of metal or polyimide film to minimize the radiative energy caused by the laser pulse from thermally damaging the bead-bound DNA.

In one embodiment, hardware is developed that is compatible with commercially available sequencers that offer high read capacities employing sequencing by synthesis with reversibly terminated dye-labeled nucleotides. This sequencing modality offers error-correction for the class of errors most common in phosphoramidite-synthesized oligonucleotides.

Figure 5:
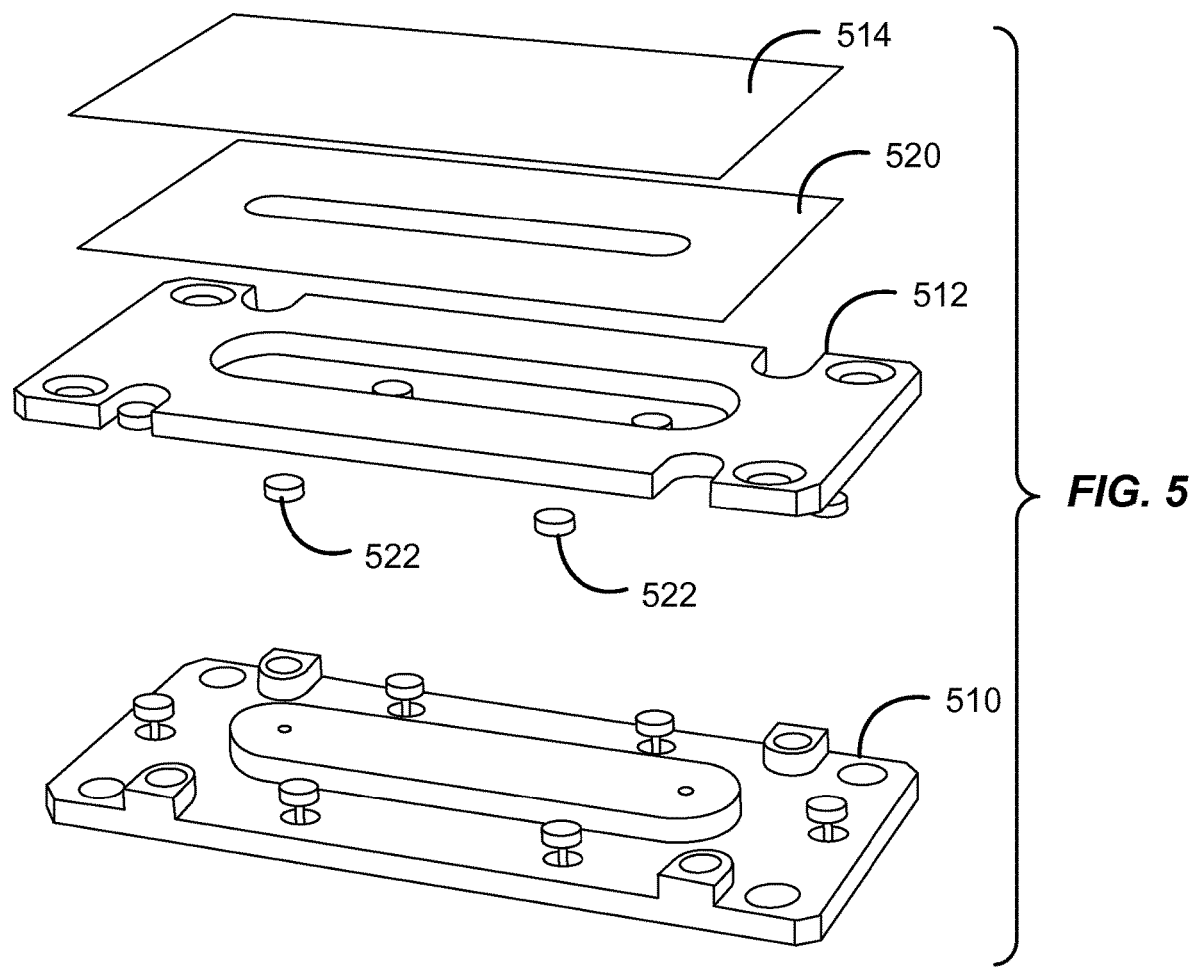
FIG. 5 is a simplified diagram illustrating a split flowcell for laser ejection, in accordance with an embodiment of the present invention.

Development of a Magnetically Assembled Flowcell System for Use in a Commercial Sequencer FIG. 5 is a simplified diagram illustrating a split flowcell for laser ejection, in accordance with an embodiment of the present invention. In one embodiment, the split flowcell includes a solid titanium base 510, an adhesive gasket layer 520 that defines a single flow-lane, and a standard glass cover-slip 514 on which emulsion-PCR amplified beads are attached. In addition, the split flowcell includes a windowed titanium holder 512, neodymium mounting magnets 522 and a titanium flowcell body. In one embodiment, the titanium flowcell is split into two parts joined via neodymium magnets while preserving the flow geometry used by the original flowcell. In one implementation, a split titanium flowcell is developed for use with Miniseq, a commercially available sequencer using Sequencing by Synthesis chemistry produced by Intelligent BioSystems (IBS).

In one embodiment, a sequencing run of a synthetic oligo fragment library with over 80% of reads yielding scores to 60 bp using the disclosed split flowcell design with standard IBS sequencing reagents may be achieved. In another embodiment, the disassembly into an open-face split component usable in a laser ejector apparatus after a successful sequencing run may also be achieved.

As will be appreciated, the mechanical design of the flowcell relates to the successful performance of a next-generation sequencer. The disclosed embodiments enable the determination of appropriate geometry and sealing mechanisms for a working flowcell compatible with SBS chemistry and laser ejection to build a cost-effective, reliable synthesis pipeline.

Design of a System for Transferring the Absolute-Positioning Coordinates of Beads Between the Sequencer and the Laser Ejection System In another embodiment, and as discussed above, embodiments of the present invention disclose techniques for co-registering bead position data from the sequencer with that of the laser ejection system. It is desirable that submicron positioning accuracy of the pulsed laser energy is achieved to accurately catapult only the desired bead (and not its neighbors). Although motion control stages of both sequencer and ejector may constrain the relative alignment to within 50-100 microns, it is desirable that quality control is achieved during the long ejection of millions of beads to quickly check and confirm the quality of laser-targeting coordinates for bead-ejection.

In one implementation, intrinsic positional information of the sequencing beads is used to perform the co-registration based on the fact that the sequencing beads are deposited randomly onto the glass coverslip, and thus themselves form a stochastic "barcode" of position. In one embodiment, noise-robust algorithms for correlating snapshots of beads to their known absolute positions from centroids extracted from sequencer raw data are disclosed. Such geometric "hashing" is a relatively fast computational task with modern computing hardware.

In another implementation, a technique to perform the co-registration includes using glass coverslips with modified surfaces carrying metal-film fiducial markings that allow direct visual co-registration of coordinate systems between the sequencer and the laser ejection system. In one embodiment, commercially available marked coverslips either in predefined patterns or tailored to custom designs may be utilized to perform the co-registration. In one implementation, this technique of co-registration may be combined with imprint patterning of the bead attachment sites in dense grids for increasing the bead density in the flowcell and thus the total number of sequenced beads for synthetic use downstream. In one embodiment, the co-registration process includes determining the affine transformation necessary to co-register bead centroid coordinates from sequencing data with the observed positions of beads in the ejector apparatus, ideally with only one or several fields of view of bright-field "bead constellations" for orientation.

Design of a Sacrificial Layer for Thermal Protection of Ejected DNA

Although it is possible to directly generate plasmas from the sequencing beads themselves or even the backing coverslip glass for creating the ejection force, this short-lived plasma has the capacity for introducing damage to the bead-bound DNA. In order to minimize this potential source for basic copy-errors in the assembly pipeline, in one embodiment, a thin sacrificial layer is applied to the sequencing coverslip in place of the bead to generate the gas pressure for ejection. In one implementation, a commercially available ~50 nm metallic thin-film coatings may be used as a sacrificial layer or alternatively an in-house spin-coated polyimide film for use as a sacrificial layer may be developed.

It is to be appreciated that the use of a sacrificial-layer enables the successful sequencing of a synthetic microarray library on flowcells. Subsequent ejection of beads using the laser ejector into a transparent substrate enables visual confirmation of minimal bead deformation/ablation. Additionally, sequencing analysis of unejected bead controls and laser-ejected beads results in a negligible statistical rate of thermally induced mutations.

Although thermal cleavage of nucleobases may not be a major error source in ejected oligonucleotides, it is desirable to minimize the thermal sources of mutation since ultimately, even infrequent mutation sources can lower the yield of perfect large-scale 10-kilobase assemblies. In one embodiment, the production of such long synthetic DNA before cloning into cells is achieved in a cost-effective manner to develop as gentle a process for DNA isolation as possible.

Implementation of a Computer-Controlled Laser Ejection System for the Rapid Sorting of Sequenced DNA In one embodiment, an optimized laser direct-write system for the rapid transfer of 1-3 micron sequencing beads from the flow cell (described in FIG. 5) at rates up to at least 1000 ejections/sec using computer-controlled motion control stages and laser-galvonometer beam-steering of a high-power Q-switched pulsed laser is implemented. In certain embodiments, a live CMOS camera imaging of bead positions is combined within the field of view for continuous calibration of absolute positioning in addition to monitoring the quality of laser catapulting. A sub-micron-accurate laser targeting for laser ejection of micron-sized beads developed in accordance with the present embodiments enables the use of a minimal set of hardware resources necessary to achieve target performance criteria, is cost effective, fast and robust.

A Custom Fixed-Bean Laser-Ejection Device Tailored for Synthesis by Sequencing

Figure 6:
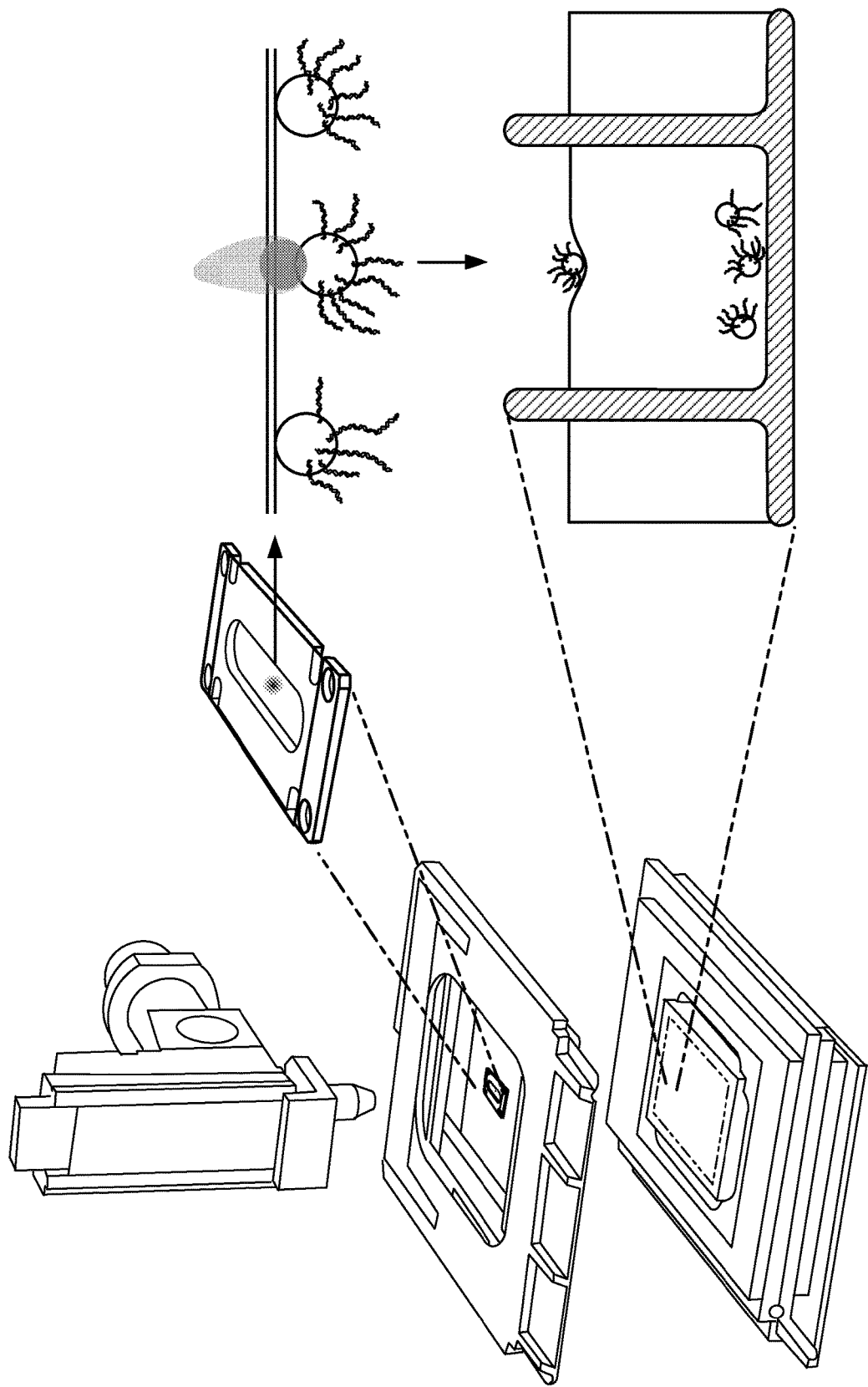
FIG. 6 is a simplified diagram illustrating a laser ejection system, in accordance with one embodiment of the present invention.
Figure 7A:
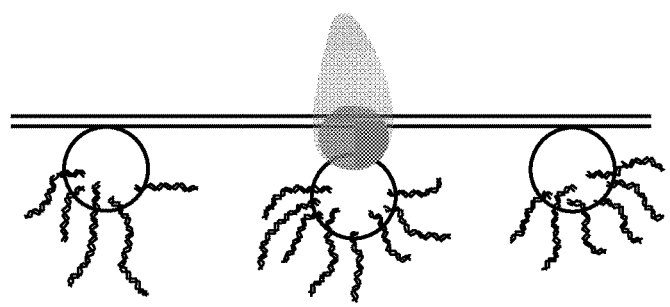
FIGS. 7A-7D are simplified diagrams illustrating hydrogel-embedded clonal clusters for use with a sequencing platform.
Figure 7B:
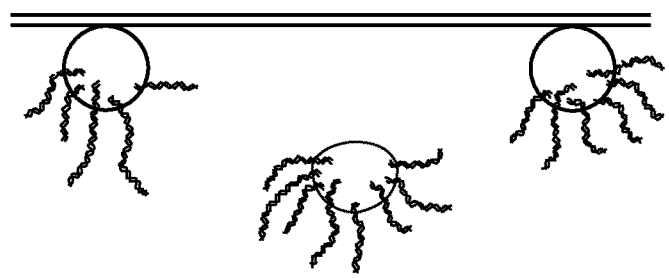
Figure 7C:
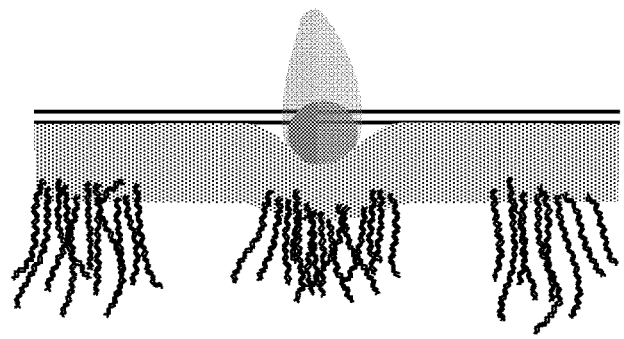
Figure 7D:
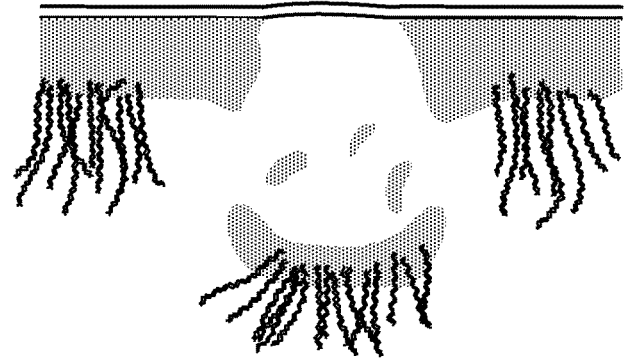

FIG. 6 is a simplified diagram illustrating a laser ejection system, in accordance with one embodiment of the present invention. The system includes an optical head incorporating autofocus and galvo-beam steering mirrors and two fast motion stages for the flowcell and collection plates. In one example, the pulsed laser ejects sequenced DNA pieces up to 1000 times a second and can sort and combine millions of sequences a day.

In one implementation, the laser ejection system is built using any commercially available modular optomechanical system known in the art. One example of a commercially available modular optomechanical system is an optomechanical system developed by Advanced Scientific Imaging (ASI) which includes a rigid framework for mounting motion-control stages, tube lenses, dichroics, cameras, and lasers in an easily adjustable configuration. In accordance with one embodiment, two sub-micron accurate motion-control stages to position both the collector 384-well plate as well as the bead-containing sequencer flowcell are used. By using brushless linear servo motors, the positioning of 5-10 beads per second at the fixed pulsed-laser focal point may be enabled. It is to be appreciated that in contrast to using commercially available microscopic rigs that typically cost several hundred thousand dollars, and include a large number of components designed for general microscopy use, the use of a laser ejection system in accordance with embodiments of the present invention is cost-effective.

In one embodiment, the ejection of one hundred DNA-labeled 3 micron beads into multiwell plates as confirmed by PCR amplification on the ejecta may be achieved. In another embodiment, an initial average ejection rate of five beads per second using software control of stages and laser switching may be achieved.

Improved system performance with a galvo-beam steered optical configuration for average performance of 100-1000 ejections/second.

In order to achieve the maximum possible throughput of sequenced oligo production, in one embodiment, a computer-controlled galvo beam-steering system to increase the number of beads ejected per second by an order of magnitude is implemented. In one embodiment, traditionally known imaging laser-scanning hardware systems are used to perform, submicron accurate positioning of laser focal points.

In one embodiment, reliable ejection of a hundred beads in a fixed field of view in less than a second using a long-range working objective may be achieved. In another embodiment, reliable ejection of a hundred beads a second while dynamically compensating for constant linear movement of the flowcell movement stage may be achieved. As will be appreciated, the construction of gene libraries may require the collection not only of a single copy of each microarray synthesized oligo, but many copies from the oversampled sequencing pool. This increases the total number of individual ejections by an order of magnitude, which may require using fast solid-state Q-switched lasers and galvo-beam steering in conjunction with the laser ejection process.

Implementation of optimal path-tracing algorithms for fast deposition of sequenced-bead sets in 384 well plates In addition to building the optomechanical hardware for targeting diffraction limited laser pulses across our sequencing flowcells, in one embodiment, an algorithm to determine the optimal path for movement of the flowcell-stage, collector-stage, and laser focal point is developed in order to sort and deposit the full collection of randomly-positioned sequencing beads into 384 well plates with a high economy of movement in a relatively short time.

In one embodiment, deposition rates of between 100,000 and 1 million beads in less than 24 hours into 384-well plates may be achieved by applying the disclosed algorithm to a set of sequenced bead positions and running the generated path on the computer-controlled ejector hardware.

Given the desired application of the laser ejector in an industrial setting for gene synthesis, it is desirable to minimize wasted movement in the system (much like the optimizations used by computer aided manufacturing software in determining optimal machining toolpaths). This helps to maximize the lifetime of the ejector's motion stages as well as minimizing the time needed to collect the full set of sequenced beads during each synthesis run.

Recovery of 384Well Plates of Sequenced, Clonally Pure 60 Mers from the Synthesis by Sequencing Pipeline In one embodiment, a system for the megabase-scale production of small synthetic DNA fragments is developed. This may generally involve adapting existing sequencing protocols for use with synthetic, as opposed to natural DNA, and using the ejected sequencing beads to demonstrate the construction of genes with the sequence-verified oligonucleotide sets created by the disclosed process. In one embodiment, production of sequence-verified linear fragments up to 1000 bp at megabase-scale per run synthesis capacity is achieved resulting in a cost-effective synthetic DNA process. In one implementation, a system for the megabase-scale production of small synthetic DNA fragments is developed by retooling existing molecular biology protocols used for sequencing and performing enzymatic assembly of DNA sequences.

Development of a Sequencing Library Preparation Method from Microarray Synthesized DNA Existing commercial sequencing sample-preparation methods have been used to process and sequence sheared fragments of larger genomic DNA. In one embodiment, the standard emulsion PCR pipeline is modified for use with the disclosed custom-synthesized microarray-synthesized DNA process. By synthesizing universal primer regions directly into the oligos, adapting DNA for sequencing may be achieved. It is to be appreciated that the development of a fast, simple sequence preparation protocol ensures that the total oligo pool is sampled uniformly at a high level of coverage (50× and above). Uniform oversampling may be critical for maximizing the success of collecting complete sets of construction oligonucleotides for each downstream assembly reaction.

In one implementation, the capture and amplification of a 12,000 oligo microarray synthesized DNA library onto 3 micron sequencing beads by emulsion PCR with 20% of beads containing DNA as confirmed by single-fluorescent nucleotide incorporation assays and direct SBS sequencing is achieved.

Demonstration of Full Collection of Sequence-Verified Oligos from a Microarray Library into 384Well Plates In one embodiment, a large set of dilute oligonucleotides that can be sequenced at high coverage redundancy and collected by laser ejection individually with one oligo per well with no detectable cross-contamination is implemented. In one embodiment, the transformation of a complex but information-rich pool of microarray oligonucleotides into an error-filtered, sorted set of oligonucleotides at concentrations directly usable for PCR-based assembly reactions using standard wetlab equipment is performed. In a specific example, a sequencing by SBS of a 50× oversampled 12,000 oligo pool and ejection of 1,000 oligos as confirmed by PCR amplification and 'spot checks' via direct Sanger resequencing is performed.

Demonstration of Feasibility of Direct One-Pot Assembly of Short Synthetic Constructs from Multiple Bead Ejecta Following the successful collection of individual beads into wells, in one embodiment, the multiple sequenced bead-bound DNA species are ejected into the same well and a set of trial PCR assembly reactions is performed on a predesigned set of test genes to verify that the ejected DNA for standard one-pot assembly reactions is suitable. It is to be appreciated that 384 well plates of pre-assembled 500-1000 bp oligonucleotides is more cost-effective than pure 60-100 bp oligonucleotides. In a specific implementation, sequencing by SBS of a 50× oversampled 12,000 oligo pool and ejection of 1,000 oligos into 30 wells of a 384 well plate followed by amplification and PCR assembly with a success rate over 70% as determined by gel electrophoresis and resequencing may be performed.

Specific Implementation Using a Sequencing Platform (e.g., from Illumina)

The present assignee employs next-generation sequencers as massively parallel sorters and quality filters of microarray-synthesized DNA. This is accomplished by transferring clonal populations of sequenced DNA from flowcells with Laser Induced Forward Transfer (LIFT). Efforts have focused on recovering DNA from platforms that employ clonal populations of DNA on beads (454, IBS/Qiagen, etc.) where effective ejection and recovery of bead-bound DNA from beads as small as 1 µm has been accomplished.

The DNA laser printing process by the present assignee can be readily adapted to work with the hydrogel-embedded clonal "clusters" used in the Illumina sequencing platforms. FIGS. 7A-7D are simplified diagrams illustrating hydrogel-embedded clonal clusters for use with a sequencing platform. To adapt the disclosed laser-ejection process and assembly pipeline to the Illumina system, a "split" version of an Illumina compatible flowcell that can be disassembled post-sequencing to expose the colonies for laser ejection is engineered.

Development of Split Flowcells for Use with Illumina Sequencers

Clamping strategies are disclosed for creating leak-free flow lanes that perform similarly to Illumina's original bonded glass lanes. The detailed design depends on whether or not the flowcell is being used on a TIRF-based sequencer such as the GAIIx or a TDI linescanning sequencer such as the HiSeq/MiSeq.

Figure 8A:
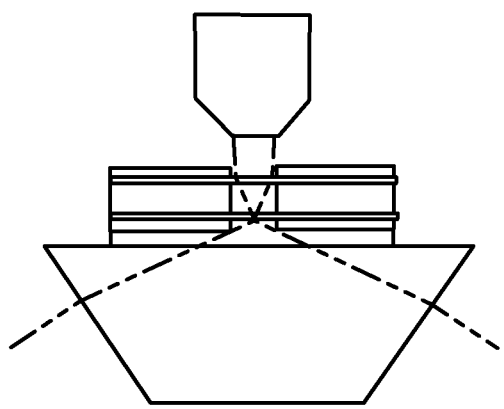
FIGS. 8A-8C are simplified diagrams illustrating a clamped flowcell for TIRF sequencers.
Figure 8B:
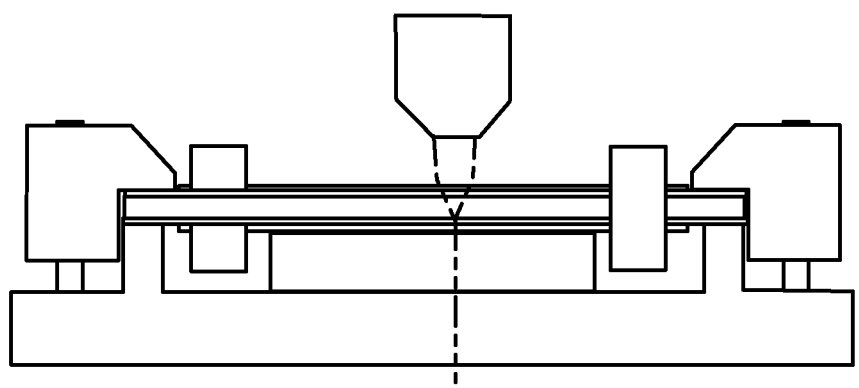
Figure 8C:
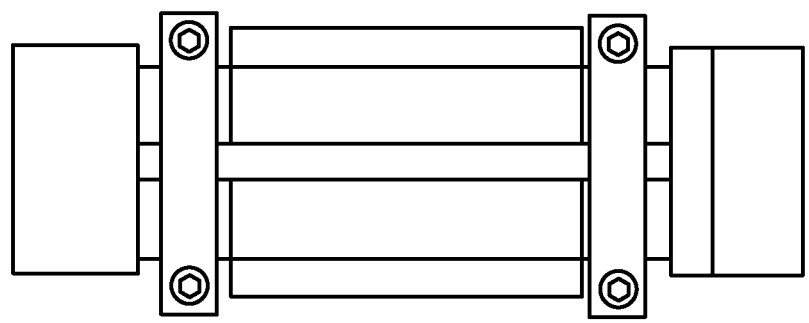

The optical design of the GAIIx uses a prism-based TIRF system to increase the signal to noise of the fluorescent signals from clusters. This may require the split flow cell to have two good optical surfaces, one coupled to the evanescent wave, and one through which fluorescence passes to the upright objective. For linescanning sequencers, only a single optical surface need be constructed, allowing for a considerably simpler design in most cases. FIGS. 8A-8C are simplified diagrams illustrating a clamped flowcell for TIRF sequencers.

The mechanically clamped design (compatible with the GAIIx mounting) uses rigid metal plates with precision machined clamps to even press two coverslips around an elastomeric spacer. It is also possible in these and other designs to use clean, optically-flat coverslip glass internally without bonding agents to define the flow lanes, provided even force is applied externally to counteract transient, differential thermal stresses during SBS cycles.

Figure 9A:
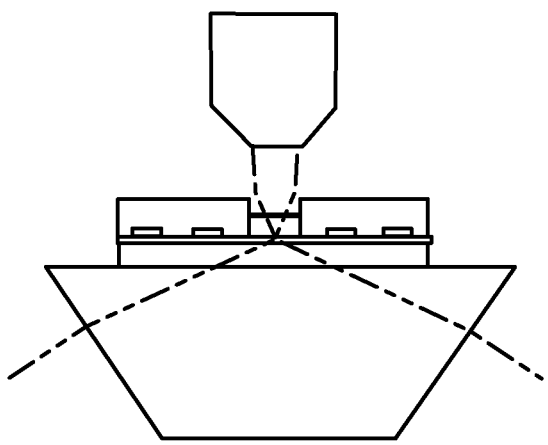
FIGS. 9A-9B are simplified diagrams illustrating a vacuum-sealed flowcell for TIRF sequencers.
Figure 9B:
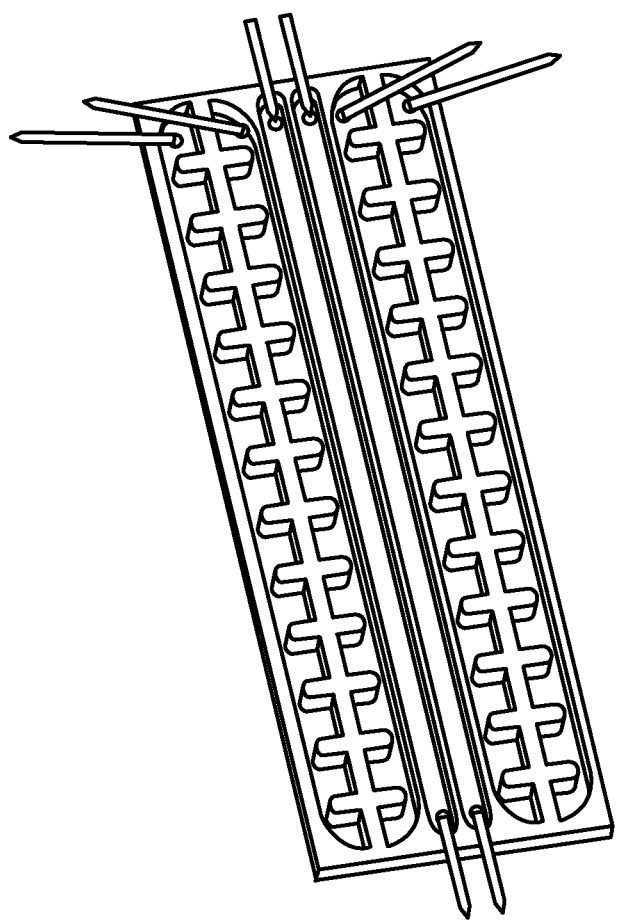

A second design uses mild negative pressure to clamp the flowcell using a vacuum-sealed flowcell. FIGS. 9A-9B are simplified diagrams illustrating a vacuum-sealed flowcell for TIRF sequencers. Given that the full capacity of a GAIIx/HiSeq flow cell may not be needed, a near-identical mechanical profile for a split flowcell may be achieved by using the existing connection manifolds to create a slight vacuum seal along well-spaced channels in the outer edges of the flowcell.

Figure 10:
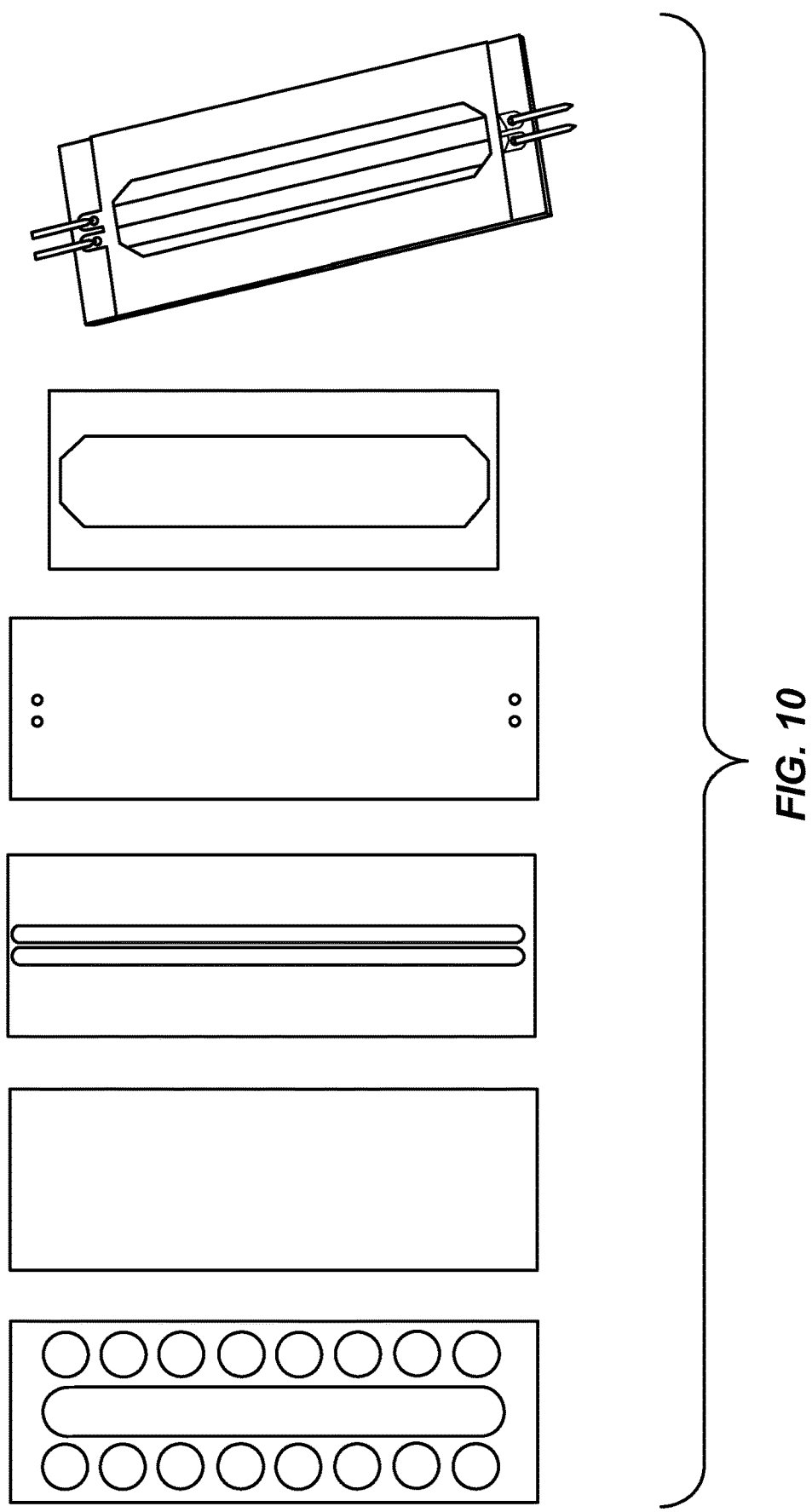
FIG. 10 is a simplified diagram illustrating a magnet-sealed flowcell.

A third design uses a magnet-sealed flowcell. In place of using a vacuum-derived force, a split flowcell of near-identical profile may operate in conjunction with GAIIx/HiSeq type sequencers by using a thin magnet clamping mechanism. FIG. 10 is a simplified diagram illustrating a magnet-sealed flowcell. Several high-Tc neodymium magnet flow cells have been developed by the present assignee that operate in conjunction in other bead-based sequencers.

Development of an Effective Ejection Protocol for Targeted Ejection of Micron-Sized DNA Clusters onto Receiver Substrates.

Methods of using emulsion-PCR derived beads by the present assignee have been based on the fact that the bead itself serves as a decent ablation substrate for the ~1 µJ nanosecond laser pulse used to induce transfer. Beads from 1 µm-10 µm are easily and specifically ejected by focusing light into their plane.

Although ejection optics disclosed by the present assignee can target features as small as ~600 nm, it desirable to generate slightly larger, more disperse 1 µm clusters for use with initial prototyping. Given that the DNA in clusters is already immobilized onto a thin hydrogel layer of linear polyacrylamide (LPA), it may be desirable to simply catapult clusters directly using the LPA as an ablative substrate. An exemplary experimental plan is discussed below:

Modify the cluster seeding density and the number of bridge PCR cycles to generate a slightly more dilute field of DNA clusters with 1 µm average diameters.

Attempt to catapult unaltered clusters via direct ablation of the hydrogel. This can be done even in the original flowcells for early tests. The experiment includes infusing the existing hydrogel with water-soluble dyes or nanoparticles for enhancing laser absorption and ablation. Ejection is tested by PCR and oligonucleotide resequencing as well as by direct visual inspection of picogreen labeled ssDNA ejecta on a fluorescence microscope. FIG. 11 is a simplified diagram illustrating a metal thin film, sacrificial layer polymer and an oligo-coupled hydrogel.

If the ejection does not prove efficient or well localized enough, a thin, vacuum sputtered 30-60 nm titanium film on the hydrogel-functionalized glass surface to act as a strong absorption layer may be used. This has been used to create localized hydrodynamic jets for small feature deposition of biological materials in the past. The use of the above approach on the GAIIx may involve the coupling of these thin metal films to the evanescent wave used in TIRF and induce surface plasmon resonances. These may potentially enhance or degrade the signal quality of the fluorescence imaging of the clusters or depending on the fluorophore properties and distance from the metal film. The disclosed embodiments perform calculations to estimate the effect and test the experimental effect on a variety of film thicknesses.

Alternatively, or especially in the case of detected DNA damage from thermal degradation during photoablation, a thin spin-coated polymer layer (such as polyimides or triazine-containing polymers) on the coverslip before functionalization with the LPA hydrogel may be used. This layer may serve as an ablation material as well as a thermal shield for the hydrogel-bound DNA.

If the above modifications to the flowcell prove suboptimal in combination with the illumina hydrogel and SBS chemistries, a simple kinematic rig to replica-plate molecular colonies from the sequencing-hydrogel plate to a separate ejection plate hydrogel using an isothermal amplification may be used. Such molecular colony replica-plating may independently optimize surface properties for SBS sequencing and laser forward transfer and guarantee good transfer with only a small decrease in cluster resolution from the additional diffusive PCR cycles.

The above goals constitute the modifications needed to adapt the disclosed pipeline to Illumina sequencers. From the ejected clusters, embodiments of the present invention may amplify the DNA species from multiple ejections to ~1 billion molecules in a microliter reaction volume scheme for batch assembly by PCR into kilobase fragments using standard protocols.

The foregoing description of the exemplary embodiments has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

It should be appreciated that the methods and systems described herein can be used in an interchangeable manner, with components and techniques utilized in one implementation also utilized in alternative implementations. One of ordinary skill in the art would recognize many variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of retrieving a subset of polynucleotide molecules from a mixture of polynucleotide molecules, the method comprising:
   receiving a mixture of nucleotide sequences comprising one or more polynucleotide molecules;
   synthesizing one or more identifier (ID) regions onto the one or more polynucleotide molecules;
   sequencing members of a population of polynucleotide molecules to associate the sequence of the one or more of the polynucleotide molecules (the "Polynucleotide Sequence") with the sequence of the one or more ID regions (the "ID Sequence");
   generating a bead-bound library of one or more beads comprising subsets of identical polynucleotide molecules, wherein each of the one or more beads is identified by the ID Sequence of the associated Polynucleotide Sequence;
   sequencing the one or more ID regions of each bead to generate ID Sequence information for each bead and to associate the ID sequence information with each bead coordinate;
   combining the Polynucleotide Sequence information, the one or more ID Sequences, and coordinates of each of the one or more beads to identify a Polynucleotide Sequence on the bead, wherein correlation between the sequencing steps is provided by the ID regions; and
   retrieving the one or more beads with their associated bead ID and variable sequence based on the absolute coordinate position of the one or more beads.

2. The method of claim 1 wherein the one or more identifier (ID) regions comprise a single identifier region having a plurality of base pairs.

3. The method of claim 2 wherein the plurality of base pairs comprise 10 or more base pairs.

4. The method of claim 3 wherein the plurality of base pairs comprise 20 or more base pairs.

5. The method of claim 1 wherein the one or more identifier (ID) regions comprise a first ID region having a first plurality of base pairs and a second ID region having a second plurality of base pairs.

6. The method of claim 5 wherein the first plurality of base pairs and the second plurality of base pairs are a different number of base pairs.

7. The method of claim 1 wherein sequencing members of the population of polynucleotide molecules to associate the sequence of the one or more of the polynucleotide molecules with the sequence of the one or more ID regions and generating a bead-bound library of one or more beads comprising subsets of identical polynucleotide molecules are performed on separate sequencers.

8. The method of claim 1 wherein the one or more beads are positioned on a flow cell.

9. A method of retrieving a subset of polynucleotide molecules from a mixture of polynucleotide molecules, the method comprising:
receiving a mixture of nucleotide sequences comprising one or more polynucleotide molecules;
synthesizing one or more identifier (ID) regions onto the one or more polynucleotide molecules;
cloning the one or more polynucleotide molecules to derive one or more subsets of identical polynucleotide molecules;
generating a bead-bound library of one or more beads comprising the one or more subsets of identical polynucleotide molecules, wherein each bead is identified by an associated bead ID and is positioned at a predetermined position;
sequencing the one or more ID regions of each bead to generate sequence information for each bead and to associate the ID region sequence information with each bead coordinate;
combining the sequence information, the one or more ID regions, and coordinates of each bead to identify a variable sequence on the bead, wherein correlation between the sequence information and the coordinates of each bead is provided by the ID regions;
determining an absolute coordinate position of the bead on a flow cell by comparing the variable sequence on the bead with a list of sequenced bead IDs in the bead-bound library; and
retrieving the bead with its associated bead ID and variable sequence from the flow cell based on the absolute coordinate position of the bead.

10. The method of claim 9 wherein sequencing the one or more ID regions of each bead is performed multiple times.

11. The method of claim 9 wherein the predetermined position is a predetermined location on a flow cell.

12. The method of claim 9 wherein generating the bead-bound library of one or more beads and sequencing the one or more ID regions of each bead are performed on different sequencers.

13. The method of claim 9 wherein the one or more ID regions comprise a random set of base pairs.

14. A method of retrieving a subset of polynucleotide molecules from a mixture of polynucleotide molecules, the method comprising:
receiving a mixture of nucleotide sequences comprising one or more polynucleotide molecules; synthesizing one or more identifier (ID) regions onto the one or more polynucleotide molecules;
sequencing members of the population of polynucleotide molecules to associate the sequence of one or more of the molecules (the "Polynucleotide Sequence") with the sequence of the attached ID region (the "ID Sequence");
generating a bead-bound library of one or more beads comprising subsets of identical polynucleotide molecules, wherein each bead is identified by the ID Sequence of the associated Polynucleotide Sequence;
sequencing the one or more ID regions of each bead to generate ID Sequence information for each bead and to associate the ID sequence information with each bead coordinate; and
retrieving the bead with its associated Polynucleotide Sequence from the flow cell based on the Polynucleotide Sequence information, the one or more ID Sequences, and coordinates of each bead, wherein correlation between the sequencing steps is provided by the ID regions.

15. The method of claim 14 wherein the bead is retrieved from a flow cell.

16. The method of claim 14 wherein the one or more ID regions comprise a random set of contiguous base pairs.

* * * * *